(12) United States Patent
Lindsey et al.

(10) Patent No.: US 9,365,722 B2
(45) Date of Patent: Jun. 14, 2016

(54) ROUTES TO TRANS A,B-SUBSTITUTED BACTERIOCHLORINS

(75) Inventors: Jonathan S. Lindsey, Raleigh, NC (US); Olga Mass, Cary, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 14/240,860

(22) PCT Filed: Aug. 24, 2012

(86) PCT No.: PCT/US2012/052273
§ 371 (c)(1),
(2), (4) Date: Mar. 31, 2014

(87) PCT Pub. No.: WO2013/062670
PCT Pub. Date: May 2, 2013

(65) Prior Publication Data
US 2014/0221644 A1    Aug. 7, 2014

Related U.S. Application Data

(60) Provisional application No. 61/527,664, filed on Aug. 26, 2011.

(51) Int. Cl.
| | |
|---|---|
| *C09B 47/00* | (2006.01) |
| *C07D 487/22* | (2006.01) |
| *C07D 405/14* | (2006.01) |

(52) U.S. Cl.
CPC .............. *C09B 47/00* (2013.01); *C07D 405/14* (2013.01); *C07D 487/22* (2013.01)

(58) Field of Classification Search
CPC ............................. C09B 47/00; C07D 405/14
USPC ........................................................ 540/145
See application file for complete search history.

(56) References Cited

U.S. PATENT DOCUMENTS

2009/0191130 A1    7/2009  Kim et al.

OTHER PUBLICATIONS

Krayer M et al. Expanded scope of synthetic bacteriochlorins via improved acid catalysis conditions and diverse dihydrodipyrrin-acetals. J Org Chem. 2010; 75(4): 1016-1039.
Hunter R. Allylation using allylborates. Tetrahedron. 1994; 50(3): 871-888.
Motokura K et al. Catalytic synthesis of homoallyloxyalcohols and 1,2-bis(homoallyloxy)ethanes through ring-opening allylation of cyclic acetals with allylsilanes over solid acids. Catal. Sci. Techol. Apr. 20, 2011; 1: 470-479.
Mass O and Lindsey JS. A trans-AB-bacteriochlorin building block. J Org Chem. Oct. 28, 2011; 76(22): 9478-9487.
International Serach Report and Written Opinion, PCT/US2012/052273, mailed Apr. 8, 2013.

*Primary Examiner* — Paul V Ward
(74) *Attorney, Agent, or Firm* — Myers Bigel & Sibley, P.A.

(57) ABSTRACT

Bacteriochlorin of Formula I: wherein R is H or silyl are described, along with compositions containing the same and methods of making and using the same.

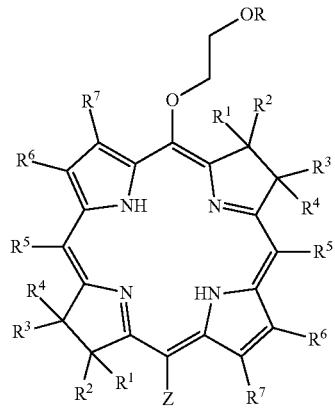

(I)

15 Claims, No Drawings

ROUTES TO TRANS A,B-SUBSTITUTED BACTERIOCHLORINS

RELATED APPLICATIONS

This application is a 35 U.S.C. §371 national phase entry of PCT Application PCT/US2012/052273, filed Aug. 24, 2012, and published in English on May 2, 2013, as International Publication No. WO 2013/062670, and which claims the benefit under 35 U.S.C. §119(e) of U.S. Provisional Patent Application Ser. No. 61/527,664, filed Aug. 26, 2011, the disclosure of each of which is incorporated herein by reference in its entirety.

STATEMENT OF FEDERAL SUPPORT

This invention was made with Government support under grant number DE-FG02-96ER14632 from the US Department of Energy. The US Government has certain rights to this invention.

FIELD OF THE INVENTION

The present invention concerns methods and intermediates for making bacteriochlorins, bacteriochlorin compounds, and tethered bacteriochlorin compounds, particularly compounds useful for near infrared applications.

BACKGROUND OF THE INVENTION

A longstanding theme in tetrapyrrole chemistry has been the de novo synthesis of building blocks for use in studies encompassing the broad fields of biomimetic chemistry, materials science, and clinical medicine. Porphyrins with up to four distinct meso-substituents are readily available.[1,2] The chemistry of chlorins is less developed, but chlorin macrocycles with substituents at designated meso- and β-pyrrole sites have been prepared.[3,4] For bacteriochlorins, synthetic access is under active development. Bacteriochlorins are of considerable interest owing to their strong absorption in the near-infrared spectral region, which is attractive for solar energy applications, low-energy photochemistry, and deep-tissue light-mediated medical therapies.[5,6] Realizing the scientific potential of bacteriochlorins has been somewhat crimped, however, by the limited means for synthesis of stable, tailorable bacteriochlorin building blocks.[7]

Distinct methods for the synthesis of bacteriochlorins entail semisynthesis procedures beginning with bacteriochlorophyll a;[8-14] hydrogenation[15,16] of (or addition to)[4,17-22] synthetic porphyrins and chlorins; and de novo routes.[5,23-28] Each has strengths and limitations. Representative building blocks available via such methods are shown in Chart 1. Derivatization of bacteriochlorophyll a to form the imide ring stabilizes the macrocycle and provides a convenient handle at the N-imide site for derivatization (entry I).[29] Still, few other sites are available given the nearly full complement of β-substituents. meso-Tetraarylbacteriochlorins (entry II) are readily synthesized yet the presence of four identical substituents may limit the accessible architectures. Two variants on this approach include (i) a strategy by Bruckner to achieve wavelength tunability,[30] and (ii) a strategy by Boyle wherein trans-AB-porphyrins undergo vicinal dihydroxylation to afford the corresponding trans-AB-bacteriochlorin building blocks (albeit composed of a mixture of diastereomers, entry III).[31]

Chart 1. Bacteriochlorophyll a and Bacteriochlorin Building Blocks

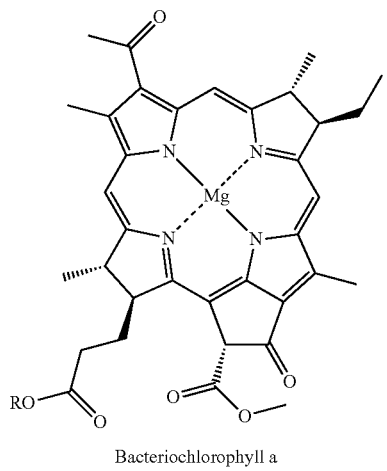

Bacteriochlorophyll a

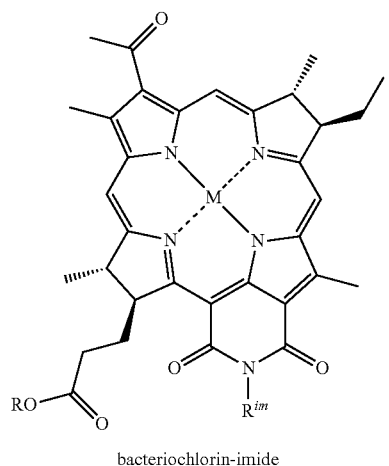

bacteriochlorin-imide

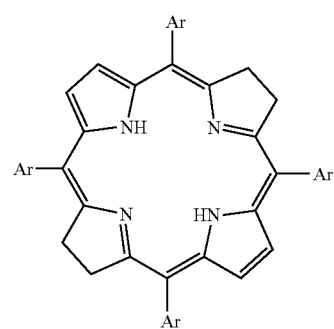

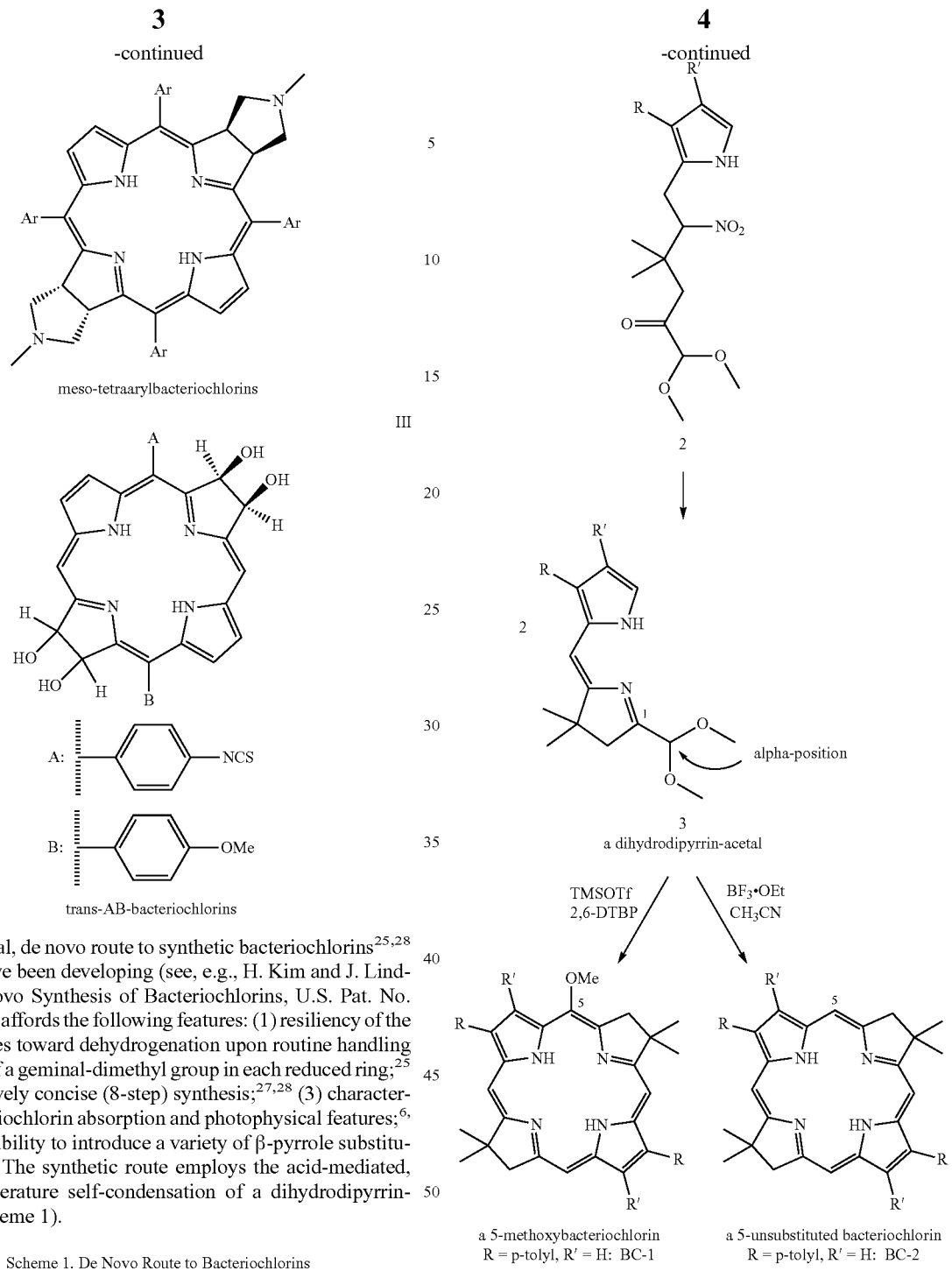

A rational, de novo route to synthetic bacteriochlorins[25,28] that we have been developing (see, e.g., H. Kim and J. Lindsey, De Novo Synthesis of Bacteriochlorins, U.S. Pat. No. 7,534,807) affords the following features: (1) resiliency of the macrocycles toward dehydrogenation upon routine handling by virtue of a geminal-dimethyl group in each reduced ring;[25] (2) a relatively concise (8-step) synthesis;[27,28] (3) characteristic bacteriochlorin absorption and photophysical features;[6,32] and (4) ability to introduce a variety of β-pyrrole substituents.[5,26,28] The synthetic route employs the acid-mediated, room-temperature self-condensation of a dihydrodipyrrin-acetal (Scheme 1).

Scheme 1. De Novo Route to Bacteriochlorins

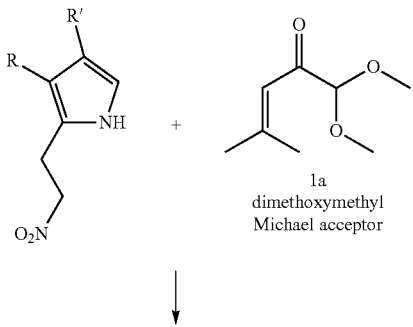

The use of TMSOTf in the presence of 2,6-di-tert-butylpyridine (2,6-DTBP) results in the formation of the 5-methoxybacteriochlorin in 8.4-63% yield depending on the nature of the β-pyrrolic substituents.[28] The 5-methoxybacteriochlorin BC-1 undergoes regioselective electrophilic bromination at the 15-position,[33] enabling further derivatization at this site via diverse palladium-coupling processes.[29,33] In contrast, bromination of the 5-unsubstituted bacteriochlorin BC-2 (available via $BF_3 \cdot OEt_2$ or other catalysis)[28] results in a mixture of mono- and dibromobacteriochlorins.[33]

While the de novo method has provided access to a larger palette of substituted bacteriochlorins versus those via semisynthesis or porphyrin/chlorin reductive transformations, numerous limitations persist: (1) the substituents at the 2- and 12-positions are identical with each other (R), as are those at the 3- and 13-position (R'); (2) the 5-methoxy group is either present or absent but otherwise not variable; and (3) approaches are not yet available to prepare trans-AB-bacteriochlorins akin to those of Boyle. A linear pattern of meso-AB-substituents is attractive for the design of various molecular architectures.

SUMMARY OF THE INVENTION

A first aspect of the present invention is a method of making a compound of Formula I:

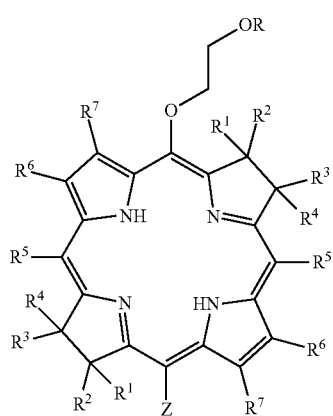

(I)

wherein:
X is selected from the group consisting of Se, NH, $CH_2$, O and S;

Z, R, $R^1$, $R^2$, $R^3$, $R^4$ $R^5$, $R^6$ and $R^7$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryl alkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, acyloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, linking groups, and surface attachment groups;

or R is silyl;
or $R^1$ and $R^2$ together are =O or spiroalkyl;
or $R^3$ and $R^4$ together are =O or spiroalkyl;

the method comprising self-condensing a compound (or condensing a pair of compounds) of Formula II:

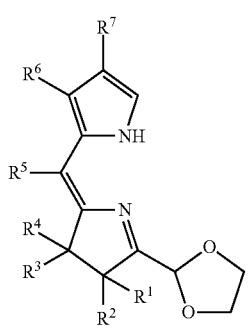

(II)

in an organic solvent in the presence of an acid to produce the compound of Formula I.

Compounds of the present invention (sometimes referred to as "active compounds" herein) include compounds of Formula I, and pharmaceutically acceptable salts, prodrugs and conjugates thereof.

A further aspect of the invention is a method for treating a target in a subject in need thereof, comprising: (i) administering to the subject the active compound as described herein or a pharmaceutically acceptable conjugate thereof that preferentially associates with the target, and (ii) irradiating the target with light of a wavelength and intensity sufficient to treat the target. Suitable subjects include but are not limited to subjects afflicted with opportunistic infections, with burns (particularly burns that have become infected), sepsis, with ulcers, periodontal disease, atherosclerosis, cosmetic and dermatologic conditions, acne, infectious diseases, tissues that require sealing such as in wounds or surgical incisions, and subjects afflicted with neoplastic disease or cancer.

A further aspect of the invention is a photodynamic therapy method for treating hyperproliferative tissue in a subject in need thereof, comprising: (i) administering to the subject an active compound as described herein or a pharmaceutically acceptable conjugate thereof that preferentially associates with the hyperproliferative tissue, and (ii) irradiating the target with light of a wavelength and intensity sufficient to activate the compound, and thereby treat the hyperproliferative tissue.

A further aspect of the invention is a method for detecting the presence of a hyperproliferative tissue in a subject, comprising: (i) administering to the subject an active compound as described herein or a pharmaceutically acceptable conjugate thereof that preferentially associates with the hyperproliferative tissue; and then (ii) visualizing the compound within the patient.

A further aspect of the present invention is a kit to treat hyperproliferative disorders, comprising the active compound described herein or a pharmaceutically acceptable conjugate thereof and instructions teaching a method of photodynamic therapy.

A further aspect of the present invention is a kit to label specific tissues for diagnosis comprising the active compound described herein or a pharmaceutically acceptable conjugate thereof and instructions teaching a method of imaging (e.g., magnetic resonance imaging).

A further aspect of the present invention is, in a method of detecting particles such as cells by flow cytometry, where the particles are labelled with a detectable luminescent compound, the improvement comprising utilizing a bacteriochlorin as described herein as the luminescent compound.

The foregoing and other objects and aspects of the invention are explained in greater detail in the drawings herein and the specification set forth below.

DETAILED DESCRIPTION OF THE PREFERRED EMBODIMENTS

"Silyl" as used herein refers to a group of the formula $-SiR^aR^bR^c$, wherein $R^a$, $R^b$, and $R^c$ are any suitable independently selected hydrocarbyl group, including but not limited to alkyl, aryl, alkylaryl, etc. Examples include, but are not limited to, trimethyl silyl, tert-butyl dimethyl silyl, etc.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Hydroxyl" as used herein refers to an —OH group.

"Nitro" as used herein refers to an —NO$_2$ group.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynynyl unless otherwise indicated and these groups may be substituted with the same groups as set forth in connection with alkyl and loweralkyl above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid as used herein refers to a compound of the formula —S(O)(O)OH.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the quaternized derivatives thereof, including but not limited to quaternary pyridyl and imidazolyl groups, examples of which include but are not limited to:

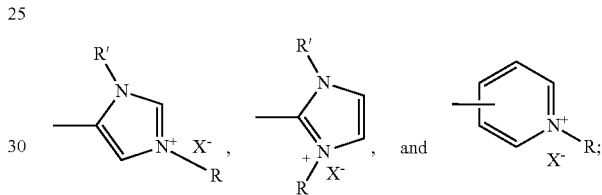

where R and R' are each a suitable substitutent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Treatment" as used herein means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated. As used herein, amelioration of the symptoms of a particular disorder by administration of a particular compound or pharmaceutical composition refers to any lessening, whether permanent or temporary, lasting or transient that can be attributed to or associated with administration of the composition.

"Prodrug" as used herein is a compound that, upon in vivo administration, is metabolized by one or more steps or processes or otherwise converted to the biologically, pharmaceutically or therapeutically active form of the compound.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Infecting agent" as used herein denotes invading microbes or parasites. As used herein, "microbe" denotes virus, bacteria, rickettsia, mycoplasma, protozoa, fungi and like microorganisms, and "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like.

"Tumor" as used herein denotes a neoplasm, and includes both benign and malignant tumors. This term particularly includes malignant tumors which can be either solid (such as a breast, liver, or prostate carcinoma) or non-solid (such as a leukemia). Tumors can also be further divided into subtypes, such as adenocarcinomas (e.g. of the breast, prostate or lung).

"Target" as used herein denotes the object that is intended to be detected, diagnosed, impaired or destroyed by the methods provided herein, and includes target cells, target tissues, and target compositions. "Target tissues" and "target cells" as used herein are those tissues that are intended to be impaired or destroyed by this treatment method. Photosensitizing compounds bind to or collect in these target tissues or target cells; then when sufficient radiation is applied, these tissues or cells are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included among target cells are cells undergoing substantially more rapid division as compared to non-target cells.

"Non-target tissues" as used herein are all the tissues of the subject which are not intended to be impaired or destroyed by the treatment method. These non-target tissues include but are not limited to healthy blood cells, and other normal tissue, not otherwise identified to be targeted.

"Target compositions" as used herein are those compositions that are intended to be impaired or destroyed by this treatment method, and may include one or more pathogenic agents, including but not limited to bacteria, viruses, fungi, protozoa, and toxins as well as cells and tissues infected or infiltrated therewith. The term "target compositions" also includes, but is not limited to, infectious organic particles such as prions, toxins, peptides, polymers, and other compounds that may be selectively and specifically identified as an organic target that is intended to be impaired or destroyed by this treatment method.

"Hyperproliferative tissue" as used herein means tissue that grows out of control and includes neoplastic tissue, tumors and unbridled vessel growth such as blood vessel growth found in age-related macular degeneration and often occurring after glaucoma surgeries.

"Hyperproliferative disorders" as used herein denotes those conditions disorders sharing as an underlying pathology excessive cell proliferation caused by unregulated or abnormal cell growth, and include uncontrolled angiogenesis. Examples of such hyperproliferative disorders include, but are not limited to, cancers or carcinomas, acute and membrano-proliferative glomerulonephritis, myelomas, psoriasis, atherosclerosis, psoriatic arthritis, rheumatoid arthritis, diabetic retinopathies, macular degeneration, corneal neovascularization, choroidal hemangioma, recurrence of pterygii, and scarring from excimer laser surgery and glaucoma filtering surgery.

"Therapeutically effective dose" as used herein is a dose sufficient to prevent advancement, or to cause regression of the disease, or which is capable of relieving symptoms caused by the disease.

"Irradiating" and "irradiation" as used herein includes exposing a subject to all wavelengths of light. Preferably, the irradiating wavelength is selected to match the wavelength(s) which excite the photosensitive compound. Preferably, the radiation wavelength matches the excitation wavelength of the photosensitive compound and has low absorption by the non-target tissues of the subject, including blood proteins.

"Biological materials" as used herein refers to both tissues (such as biopsy tissues) and cells, as well as biological fluids such as blood, urine, plasma, cerebrospinal fluid, mucus, sputum, etc.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

While one preferred embodiment of the present invention is drawn to the use of light energy for administering photodynamic therapy (PDT) to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical, and electrical. For example, sonodynamically induced or activated agents include, but are not limited to: gallium-porphyrin complex (see Yumita et al., Cancer Letters 112: 79-86 (1997)), other porphyrin complexes, such as protoporphyrin and hematoporphyrin (see Umemura et al., Ultrasonics Sonochemistry 3: S187-S191 (1996)); other cancer drugs, such as daunorubicin and adriamycin, used in the presence of ultrasound therapy (see Yumita et al., Japan J. Hyperthermic Oncology 3(2):175-182 (1987)).

"Coupling agent" as used herein, refers to a reagent capable of coupling a photosensitizer to a targeting agent "Targeting agent" refers to a compound that homes in on or preferentially associates or binds to a particular tissue, receptor, infecting agent or other area of the body of the subject to be treated, such as a target tissue or target composition. Examples of a targeting agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-.alpha. and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

Subjects to be treated by the methods of the present invention for diagnostic or therapeutic purposes include both human subjects and animal subjects (particularly mammalian subjects such as dogs, cats, horses, monkeys, chimpanzees, etc.) for veterinary purposes.

The disclosures of all United States Patent references cited herein are to be incorporated by reference herein as if fully set forth.

1. Compounds and Methods of Making.

As noted above, an aspect of the present invention is a method of making a compound of Formula I:

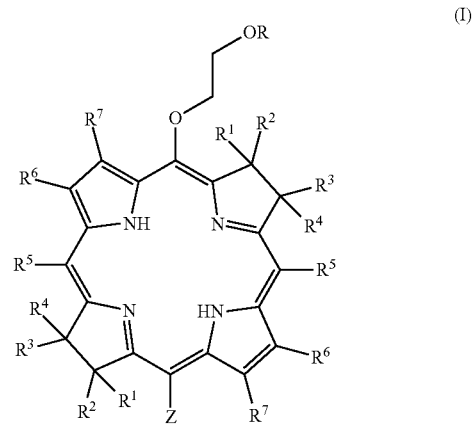

wherein:

X is selected from the group consisting of Se, NH, $CH_2$, O and S;

R, Z, $R^1$, $R^2$, $R^3$, $R^4$ $R^5$, $R^6$ and $R^7$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, linking groups, and surface attachment groups;

or $R^1$ and $R^2$ together are =O or spiroalkyl (in which case preferably neither $R^3$ nor $R^4$ is H);

or $R^3$ and $R^4$ together are =O or spiroalkyl (in which case preferably neither R' nor $R^2$ is H);

the method comprising self-condensing a compound (or condensing a pair of compounds) of Formula II:

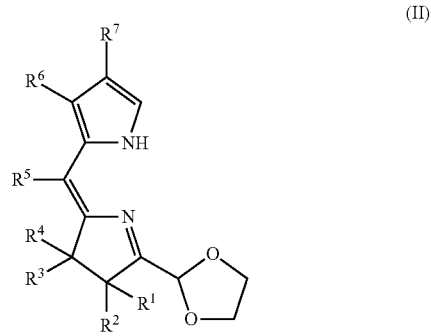

in an organic solvent in the presence of $CF_3SO_3R$, wherein R is silyl, to produce the compound of Formula I, wherein R is silyl, Z is H, and $R^1$ to $R^7$ are as given above.

It will be appreciated that when a single compound is self-condensed, the various groups $R^1$ through $R^7$ will be symmetric in the compounds of Formula I, but that when a pair of compounds with different patterns of substituents are condensed, the various groups $R^1$ through $R^7$ may be unsymmetric or different in the compounds of Formula I).

In some embodiments, $R^1$, $R^2$, $R^3$, and $R^4$ are preferably each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, alkoxy, carboxylic acid, hydroxyl, alkylthio, amino, alkylamino, arylalkylamino, disubstituted amino, acylamino, acyloxy, ester, In some embodiments, $R^1$, $R^2$, $R^3$, and $R^4$ are most preferably each independently selected from the group consisting of H and alkyl.

In some embodiments, preferably, $R^1$ and $R^2$ are each independently selected from the group consisting of H, alkyl, cycloalkyl, aryl, alkoxy, halo, mercapto, hydroxyl, nitro, acyl, alkoxy, alkylthio, amino, alkylamino, arylalkylamino, disubstituted amino, acylamino, acyloxy, amide, sulfonamide, urea, alkoxylacylamino, aminoacyloxy, and linking groups. Most preferably $R^1$ and $R^2$ are each independently selected from the group consisting of H, alkyl, aryl, alkoxy, halo, mercapto, cyano, hydroxyl, nitro, acyl, alkoxy, alkylthio, alkylamino, acyloxy, amide, and linking groups. In some embodiments $R^1$ and $R^2$ are preferably not H, alkyl or cycloalkyl ("cycloalkyl" including heterocyclo), particularly not alkyl or cycloalkyl, and most particularly one is not alkyl when the other is cycloalkyl.

In some embodiments, preferably, $R^3$ and $R^4$ are each independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups. Most preferably, $R^3$ and $R^4$ are each independently selected from the group consisting of alkyl, cycloalkyl, aryl, arylalkyl, and linking groups.

In some embodiments, preferably, $R^5$ is selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, cyano, nitro, acyl, alkoxy, alkylthio, amino, alkylamino, arylalkylamino, disubstituted amino, acylamino, acyloxy, amide, sulfonamide, urea, alkoxylacylamino, aminoacyloxy, and linking groups. Most preferably, $R^5$ is selected from the group consisting of H, alkyl, alkenyl, alkynyl, cycloalkyl, aryl, arylalkyl, arylalkenyl, arylalkynyl, alkoxy, halo, cyano, nitro, acyl, alkoxy, alkylthio, alkylamino, arylalkylamino, disubstituted amino, acylamino, acyloxy, amide, and linking groups.

In some embodiments $R^5$ is preferably not H or alkyl, and particularly not H.

In some embodiments, preferably, $R^6$ and $R^7$ are each independently selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, cyano, nitro, acyl, alkoxy, alkylthio, amino, alkylamino, arylalkylamino, disubstituted amino, acylamino, acyloxy, amide, sulfonamide, urea, alkoxylacylamino, aminoacyloxy, and linking groups. Most preferably, $R^6$ and $R^7$ are each independently selected from the group consisting of H, alkyl, alkenyl, alkynyl, cycloalkyl, aryl, arylalkyl, arylalkenyl, arylalkynyl, alkoxy, halo, cyano, nitro, acyl, alkoxy, alkylthio, alkylamino, arylalkylamino, disubstituted amino, acylamino, acyloxy, amide, and linking groups.

In some embodiments at least one or both $R^6$ is preferably neither H nor alkyl, and particularly not H.

In some embodiments at least one or both $R^7$ is preferably neither H nor alkyl, and particularly not methyl.

Compounds of Formula I are made from compounds of Formula II by treating the compounds of Formula II with an acid in an organic solvent. The acid is preferably $CF_3SO_3R$, wherein R is silyl such as trimethylsilyl. The organic solvent is not critical with examples including but not limited to acetonitrile, methylene chloride, chloroform, tetrahydrofuran, chlorobenzene, ethanol, and combinations thereof. The reaction may be carried out at any suitable temperature, such as 0 to 100° C., and conveniently at room temperature, for any suitable time period, such as for a few minutes, 1 to 4 hours, or a day. The reaction mixture is preferably nonaqueous but need not be anhydrous, and may conveniently be carried out exposed to air.

Once formed, the silyl group at substituent R in the compounds of Formula I can be cleaved to convert R to H in accordance with known techniques. In some embodiments, cleavage is carried out by combining the compound of Formula I with a fluorine source or fluoride reagent in a solvent. Reaction conditions are not critical and will be apparent to those skilled in the art. Examples of suitable fluoride reagents include, but are not limited to, NaF, KF, CsF, tetrabutylammonium fluoride, and supported fluoride reagents such as fluoride on a solid substrate such as alumina or Celite. Suitable solvents include, but are not limited to, hydrocarbons and ethereal solvents such as tetrahydrofuran.

H can in turn be converted to any of a variety of other substituents by known techniques as discussed further below. The conditions for halogenation are known to those skilled in the art or will be apparent in view of the disclosure herein. The halogenation methods include the use of reagents to introduce fluorine, chlorine, bromine, and iodine, with bromine and iodine preferred. Typical reagents include N-fluoropyridinium triflate, cesium fluoroxysulfate, $F_2$, $CF_3OF$, $ClF_3$, $Cl_2$/$FeCl_3$, thionyl chloride, $AgPF_6$/iodine, $Br_2$, N-bromosuccinimide (NBS), N-bromoacetamide, $I_2$, N-iodosuccinimide (NIS), N-iodoacetamide, and similar reagents. The reaction is believed to entail electrophilic aromatic substitution (rather than free radical substitution) and hence reagents and conditions that facilitate formation and reaction of the electrophilic halogen species are preferred. Solvents for halogenation include those that afford non-acidic (i.e., neutral or basic) conditions. The presence of Bronsted acids upon protonation of the bacteriochlorin would deactivate the bacteriochlorin toward electrophilic substitution. Solvents that are suitable include pyridine, ethers (e.g., tetrahydrofuran) or chlorinated hydrocarbons ($CCl_4$, $CHCl_3$, trichloroethane). A base can be included if desired to neutralize any acid (HX where X=halogen) liberated in the reaction. Suitable bases include triethylamine, diisopropylethylamine, tributylamine. In some embodiments an acid can be added, for example $CH_2Cl_2$ containing trifluoroacetic acid. The halogenation often is carried out under conditions that at initiation are cryogenic but then are allowed to warm over time. Examples include initiation of the reaction (by addition of the halogenation reagent) to all other reaction constituents at −78 C and then allowing the reaction mixture to warm to room temperature. Lower temperatures (e.g., −150 C) can be employed at the outset and warmer temperatures (e.g., +150 C) can be employed to finish the reaction. The addition of the halogenation reagent can be done all-at-once, in portions, or by steady addition (addition funnel if solid, syringe pump if liquid).

Compounds of Formula I may be metalated with any suitable metal in accordance with known techniques. See, e.g., U.S. Pat. No. 6,208,553. Suitable metals include but are not limited to Pd(II), Pt(II), Mg(II), Zn(II), Al(III), Ga(III), In(III), Sn(IV), Cu(II), Ni(II), and Au(III). Where the metal is trivalent or tetravalent a counterion is included as necessary in accordance with known techniques.

Linking Groups for Conjugates.

Linking groups are included in compounds of Formula I to provide a reactive site for conjugation so that the compounds may be coupled to or conjugated to other groups such as proteins, peptides, targeting agents such as antibodies, polymers, particles such as nanoparticles, organic, polymeric or inorganic beads, other solid support surfaces, etc., to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R' is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidinium, pyridinium). Bioconjugatable groups include amines (including amine derivatives) such as isocyanates, isothiocyanates, iodoacetamides, azides, diazonium salts, etc. acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Linking groups such as the foregoing are known and described in U.S. Pat. Nos. 6,728,129; 6,657,884; 6,212,093; and 6,208,553.

Conjugates.

Other groups can be attached to the bacteriochlorin to form a conjugate by means of a linking group to tune or adjust the solubility properties of the bacteriochlorin, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc. may be attached by means of the linking group. Where such additional compounds are attached to form a conjugate that may be attached directly to the bacteriochlorin or attached by means of an intervening group such as a hydrophilic group, depending upon the particular linking group employed (as noted above).

Hydrophilic Groups.

Compounds of the present invention may include hydrophilic groups coupled at the linking sites noted above, e.g., covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to polypropylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group.

Surface Attachment Groups.

As noted above, compounds of the invention can be substituted with a surface attachment group, which may be in protected or unprotected form. A surface attachment group may be a reactive group coupled directly to the bacteriochlorin, or coupled to the bacteriochlorin by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to alkene, alkyne, alcohol, thiol, selenyl, phosphono, telluryl, cyano, amino, formyl, halo, boryl, and carboxylic acid surface attachment groups such as:

4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl)ethynyl) phenyl; 4-hydroxyphenyl, hydroxymethyl, 2-hydroxyethyl, 3-hydroxypropyl, 2-(4-hydroxyphenyl)ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl)ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl)ethynyl) phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl; 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl,2-tellurylethyl,3-tellurylpropyl, 2-(4-tellurylphenyl)ethynyl, 4-(2-(4-tellurylphenyl) ethynyl)phenyl, 4-tellurylmethylphenyl, 4-(2-tellurylethyl) phenyl, 4-(3-tellurylpropyl)phenyl, 4-(2-(4-tellurylmethylphenyl)ethynyl)phenyl;

4-(dihydroxyphosphoryl)phenyl, (dihydroxyphosphoryl) methyl,2-(dihydroxyphosphoryl)ethyl, 3-(dihydroxyphosphoryl)propyl, 2-[4-(dihydroxyphosphoryl)phenyl]ethynyl, 4-[2-[4-(dihydroxyphosphoryl)phenyl]ethynyl]phenyl, 4-[(dihydroxyphosphoryl)methyl]phenyl, 4-[2-(dihydroxyphosphoryl)ethyl]phenyl, 4-[2-[4-(dihydroxyphosphoryl) methylphenyl]ethynyl]phenyl; 4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-(hydroxy(mercapto)phosphoryl)phenyl]ethynyl, 4-[2-[4-(hydroxy(mercapto)phosphoryl)phenyl]ethynyl]phenyl, 4-[(hydroxy(mercapto) phosphoryl)methyl]phenyl, 4-[2-(hydroxy(mercapto) phosphoryl)ethyl]phenyl, 4-[2-[4-(hydroxy(mercapto) phosphoryl)methylphenyl]ethynyl]phenyl;

4-cyanophenyl, cyanomethyl, 2-cyanoethyl, 3-cyanopropyl, 2-(4-cyanophenyl)ethynyl, 4-[2-(4-cyanophenyl)ethynyl]phenyl, 4-(cyanomethyl)phenyl, 4-(2-cyanoethyl)phenyl, 4-[2-[4-(cyanomethyl)phenyl]ethynyl]phenyl;

4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl;

4-formylphenyl, 4-bromophenyl, 4-iodophenyl, 4-vinylphenyl, 4-ethynylphenyl, 4-allylphenyl, 4-[2-(trimethylsilyl)ethynyl]phenyl, 4-[2-(triisopropylsilyl)ethynyl]phenyl,4-(4,4,5,5-tetramethyl-1,3,2-dioxaborolan-2-yl)phenyl;

formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl;

4-(bromomethyl)phenyl, and 2-bromoethyl.

In addition to the monodentate linker-surface attachment groups described above, multidentate linkers can be employed [Nikitin, K. *Chem. Commun.* 2003, 282-283; Hu, J.; Mattern, D. L. *J. Org. Chem.* 2000, 65, 2277-2281; Yao, Y.; Tour, J. M. *J, Org. Chem.* 1999, 64, 1968-1971; Fox, M. A. et al. *Langmuir,* 1998, 14, 816-820; Galoppini, E.; Guo, W. *J. Am. Chem. Soc.* 2001, 123, 4342-4343; Deng, X, et al. *J. Org. Chem.* 2002, 67, 5279-5283; Hector Jr., L. G. et al. *Surface Science,* 2001, 494, 1-20; Whitesell, J. K.; Chang, H. K. *Science,* 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphoric acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl]
methyl}phenyl,
1,1,1-tris[4-dihydroxyphosphorylmethyl)phenyl]methyl, and
4-{1,1,1-tris[4-(dihydroxyphosphorylmethyl)phenyl]
methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to:

Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.
Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4'-yl,
Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc., Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc., Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.

Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc and Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Active compounds of the invention can be provided as pharmaceutically acceptable salts. Such salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Active compounds of the invention include prodrugs of the compounds described herein. As noted above, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Utility.

The methods and intermediates described herein are useful for the synthesis of compounds of Formula I as described herein. Such compounds are useful per se or in further modified form (e.g., as a salt, metalated compound, conjugate or prodrug) for diagnostic and therapeutic purposes in like manner as other compounds described for photodynamic therapy, such as described in US Patent Application Publication No. 2004/0044197 to Pandey et al. and as set forth in further detail below.

Stability.

An advantage of the compounds of the present invention is their stability and absorption characteristics. Thus, the present invention provides a "neat" composition consisting of an active compound of the invention (e.g., compounds of Formula I, or the pharmaceutically acceptable salts, prodrugs, or conjugates thereof (e.g, with a targeting agent such as a protein, peptide or antibody)), wherein the composition has or is characterized by a peak Molar absorption coefficient in solution of at least 10,000, up to 300,000 $M^{-1}$ $cm^{-1}$ or more, at a wavelength between 650 and 850 or 900 nanometers (it being understood that (a) the active compound must be placed into solution to determine its peak Molar absorption coefficient at the indicated wavelength; and (b) the compound may exhibit additional peaks outside of this range, or multiple peaks within this range).

In addition, the present invention provides compositions comprising or consisting essentially of an active compound of the invention (e.g., compounds of Formula I, or the pharmaceutically acceptable salts, prodrugs, or conjugates thereof (e.g, with a targeting agent such as a protein, peptide or antibody)) in a solvent. The amount of solvent is not critical and may comprise from 0.01 or 1 to 99 or 99.99 percent by weight of the composition. The composition has or is characterized by a peak Molar absorption coefficient in solution of at least 10,000, up to 300,000 $M^{-1}$ $cm^{-1}$ or more, at a wavelength between 650 and 850 or 900 nanometers. It will be appreciated that agitation may be required to break agglomerated particles back into solution prior to determining molar absorption, but that some level of agglomeration may actually be desired for practical use of the composition. Suitable solvents depend upon the particular compound and intended use for that compound, but include both organic solvents, aqueous solvents and combinations thereof.

The compositions, be they the bacteriochlorin compounds in "neat" form or the compounds mixed with a solvent, have or exhibit a loss of not more than 10, 15 or 20 percent by weight of the bacteriochlorin compound of the invention (due to degradation thereof) when stored in a sealed vessel (e.g., a flask ampoule or vial), at room temperature in the absence of ambient light for at least 3 or 4 months. Degradation can be determined by spectroscopy, thin-layer chromatography, NMR spectroscopy, and/or mass spectrometry, in accordance with known techniques.

2. Pharmaceutical Formulations.

Formulation of Pharmaceutical Compositions.

The pharmaceutical compositions provided herein contain therapeutically effective amounts of one or more of the compounds provided herein that are useful in the prevention, treatment, or amelioration of one or more of the symptoms of diseases or disorders associated with hyperproliferating tissue or neovascularization, or in which hyperproliferating tissue or neovascularization is implicated, in a pharmaceutically acceptable carrier. Diseases or disorders associated with hyperproliferating tissue or neovascularization include, but are not limited to, cancer, psoriasis, atherosclerosis, heart disease, and age-related macular degeneration. Pharmaceutical carriers suitable for administration of the compounds provided herein include any such carriers known to those skilled in the art to be suitable for the particular mode of administration.

Pharmaceutical compositions preferably exhibit the absorption characteristics and storage or stability characteristics described above.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with hyperproliferating tissue or neovascularization or in which hyperproliferating tissue or neovascularization is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with hyperproliferating tissue or neovascularization or in which hyperproliferating tissue or neovascularization is implicated, as described herein.

In one embodiment, a therapeutically effective dosage should produce a serum concentration of active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Compositions for Oral Administration.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration.

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient. When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wefting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

3. Injectables, Solutions and Emulsions.

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, xanthan gum, hydroxypropyl methylcellulose and polyvinylpyrrolidone. Emulsifying agents include Polysorbate 80 (TWEEN™ 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders.

Lyophilized powders, which can be reconstituted for administration as solutions, emulsions and other mixtures, can also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Compositions for Other Routes of Administration.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983; 6,261,595; 6,256,533; 6,167,301; 6,024,975; 6,010715; 5,985,317; 5,983,134; 5,948,433 and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations.

The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

Liposomes.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Ligands.

In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, can be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Esherichia coli, Neisseria gonorrhosae, Neisseria meningitidis, Pneumococcus, Hemophilis influenzae* B, *Treponema pallidum*, Lyme disease, spirochetes, *Pseudomonas aeruginosa, Mycobacterium leprae, Brucella abortus, Mycobacterium tuberculosis*, Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis, Taenia saginata*, Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus, Antimycoplasmal MAbs such as those against *Acholeplasma laidlawii, Mycoplasma arthritidis, M. hyorhinis, M. orale, M. arginini, M. pneumonia*; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, are appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to *T. gondii*, the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating target tissue and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include $F(ab')_2$, $F(ab)_2$, Fab', Fab, Fv and the like including hybrid fragments. Preferred fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin.

A ligand or one member of a ligand-receptor binding pair can be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Conjugation to Ligands.

Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorin e via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein can also be conjugated to a ligand, such as an antibody, by using a coupling agent. Any bond which is capable of linking the components such that they are stable under physiological conditions for the time needed for administration and treatment is suitable, but covalent linkages are preferred. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester.

Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies can be prepared by coupling the compound to targeting moieties by cleaving the ester on the "d" ring and coupling the compound via peptide linkages to the antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-S-acetyl-thioacetate (SATA), N-succinimidyl-3-(2-pyridyidi-thio)propionate (SPDP), ortho-phenylene-dimaleimide (o-PDM), and sulfosuccinimidyl 4-(N-maleimido-methyl)-cyclohexane-1-carboxylate (sulfo-SMCC). See, e.g., Karpovsky et al. J. Exp. Med. 160:1686 (1984); and Liu, M A et al., Proc. Natl. Acad. Sci. USA 82: 8648 (1985). Other methods include those described by Brennan et al. Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages O-90 to O-110 (1995, Pierce Chemical Co., 3747 N. Meridian Rd., Rockford Ill., 61105, U.S.A.), which catalog is hereby incorporated by reference.

For example, DCC is a useful coupling agent that can be used to promote coupling of the alcohol NHS to chlorin e6 in DMSO forming an activated ester which can be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizers which contain carboxyl groups can be joined to lysine s-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. B. et al., Ciba Found Symp. 186: 5-20 (1994).

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which hyperproliferating tissue or neovascularization is implicated as a mediator or contributor to the symptoms or cause.

3. Methods of Use.

A. Methods of PDT, Diagnostic and Therapeutic Applications.

Briefly, the photosensitizing compound is generally administered to the subject before the target tissue, target composition or subject is subjected to illumination. The photosensitizing compound is administered as described elsewhere herein.

The dose of photosensitizing compound can be determined clinically. Depending on the photosensitizing compound used, an equivalent optimal therapeutic level will have to be established. A certain length of time is allowed to pass for the circulating or locally delivered photosensitizer to be taken up by the target tissue. The unbound photosensitizer is cleared from the circulation during this waiting period, or additional time can optionally be provided for clearing of the unbound compound from non-target tissue. The waiting period will be determined clinically and may vary from compound to compound.

At the conclusion of this waiting period, a laser light source or a non-laser light source (including but not limited to artificial light sources such as fluorescent or incandescent light, or natural light sources such as ambient sunlight) is used to activate the bound drug. The area of illumination is determined by the location and dimension of the pathologic region to be detected, diagnosed or treated. The duration of illumination period will depend on whether detection or treatment is being performed, and can be determined empirically. A total or cumulative period of time anywhere from between about 4 minutes and 72 hours can be used. In one embodiment, the illumination period is between about 60 minutes and 148 hours. In another embodiment, the illumination period is between about 2 hours and 24 hours.

Preferably, the total fluence or energy of the light used for irradiating, as measured in Joules, is between about 10 Joules and about 25,000 Joules; more preferably, between about 100 Joules and about 20,000 Joules; and most preferably, between about 500 Joules and about 10,000 Joules. Light of a wavelength and fluence sufficient to produce the desired effect is selected, whether for detection by fluorescence or for therapeutic treatment to destroy or impair a target tissue or target composition. Light having a wavelength corresponding at least in part with the characteristic light absorption wavelength of the photosensitizing agent is preferably used for irradiating the target issue.

The intensity or power of the light used is measured in watts, with each Joule equal to one watt-sec. Therefore, the intensity of the light used for irradiating in the present invention may be substantially less than 500 mW/cm$^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent.

In one embodiment of using compounds disclosed herein for photodynamic therapy, the compounds are injected into the mammal, e.g. human, to be diagnosed or treated. The level of injection is usually between about 0.1 and about 0.5 umol/kg of body weight. In the case of treatment, the area to be treated is exposed to light at the desired wavelength and energy, e.g. from about 10 to 200 J/cm$^2$. In the case of detection, fluorescence is determined upon exposure to light at a wavelength sufficient to cause the compound to fluoresce at a wavelength different than that used to illuminate the compound. The energy used in detection is sufficient to cause fluorescence and is usually significantly lower than is required for treatment.

Any one of the photosensitizing compounds disclosed herein or a pharmaceutically acceptable derivative thereof may be supplied in a kit along with instructions on conducting any of the methods disclosed herein. Instructions may be in any tangible form, such as printed paper, a computer disk that instructs a person how to conduct the method, a video cassette containing instructions on how to conduct the method, or computer memory that receives data from a remote location and illustrates or otherwise provides the instructions to a person (such as over the Internet). A person may be instructed in how to use the kit using any of the instructions above or by receiving instructions in a classroom or in the course of treating a patient using any of the methods disclosed herein, for example.

Additional examples and specific examples of methods of using compounds and compositions of the present invention include but are not limited to the following:

(i) Treatment of Opportunistic Infections.

Compounds, compositions and methods of the invention are useful for PDT of opportunistic infections, particularly of soft tissue. For antimicrobial treatment (via PDT) of infections, particularly wound infections, the infecting organism can include (as non limiting examples) *Staphylococcus aureus, Pseudomonas aeruginosa, Escherichia coli*. In nosocomial infections, *P. aeruginosa* is responsible for 8% of surgical-wound infections and 10% of bloodstream infections. In some embodiments the subjects are immunocompromised subjects, such as those afflicted with AIDS or undergoing treatment with immunosupressive agents.

(ii) Treatment of Burns.

Infections by *S. aureus* and gram-positive bacteria in general are particularly pronounced in burns (Lambrechts, 2005). The multidrug resistance of *S. aureus* presents significant medical challenges. In this regard, compounds, compositions and methods of the invention are useful for the treatment of opportunistic infections of burns.

(iii) Sepsis.

Compounds, compositions and methods of the invention are useful for the PDT treatment of subjects afflicted with opportunistic infections of *Vibrio vulnificus*. *V. vulnificus*, a gram-negative bacterium, causes primary sepsis, wound infections, and gastrointestinal illness in humans.

(iv) Ulcers.

Compounds, compositions and methods of the invention are useful for PDT treatment of the bacterium that causes ulcers (*Helicobacter pylori*). In the clinic, treatment can be effected in any suitable manner, such as by insertion of a fiber optic cable (akin to an endoscope but with provisions for delivery of red or near-IR light) into the stomach or afflicted region.

(v) Periodontal Disease.

Compounds, compositions and methods of the invention are useful in PDT for the treatment of periodontal disease, including gingivitis. Periodontal disease is caused by the overgrowth of bacteria, such as the gram-negative anaerobe *Porphyromonas gingivalis*. As with many PDT treatments, targeting or solubilizing entities in conjunction with the photoactive species are essential for appropriate delivery of the photoactive species to the desired cells. The oral pathogens of interest for targeting include *Porphyromonas gingivalis, Actinobacillus actinomycetemcomitans, Bacteroides forsythus, Campylobacter rectus, Eikenella corrodens, Fusobacterium nucleatum* subsp. *Polymorphum, Actinomyces viscosus*, and the streptococci. For such applications the compounds or compositions of the invention can be topically applied (e.g., as a mouthwash or rinse) and then light administered with an external device, in-the-mouth instrument, or combination thereof.

(vi) Atherosclerosis.

Compounds, compositions and methods of the invention are useful in PDT to treat vulnerable atherosclerotic plaque. Without wishing to be bound to any particular theory, invading inflammatory macrophages are believed to secrete metalloproteinases that degrade a thin layer of collagen in the coronary arteries, resulting in thrombosis, which often is lethal (Demidova and Hamblin, 2004). Bacteriochlorins targeted to such inflammatory macrophages are useful for PDT of vulnerable plaque.

(vii) Cosmetic and Dermatologic Applications.

Compounds, compositions and methods of the invention are useful in PDT to treat a wide range of cosmetic dermatological problems, such as hair removal, treatment of psoriasis, or removal of skin discoloration. Ruby lasers are currently used for hair removal; in many laser treatments melanin is the photosensitized chromophore. Such treatments work reasonably well for fair-skinned individuals with dark hair. Compounds, compositions and methods of the invention can be used as near-IR sensitizers for hair removal, which enables targeting a chromophore with a more specific and sharp absorption band.

(viii) Acne.

Compounds, compositions and methods of the invention are useful in PDT to treat acne. Acne *vulgaris* is caused by *Propionibacterium acnes*, which infects the sebaceous gland; some 80% of young people are affected. Here again, the growing resistance of bacteria to antibiotic treatment is leading to an upsurge of acne that is difficult to treat. Current PDT treatments of acne typically rely on the addition of aminolevulinic acid, which in the hair follicle or sebaceous gland is converted to free base porphyrins. Compounds and compositions of the invention can be administered to subjects topically or parenterally (e.g., by subcutaneous injection) depending upon the particular condition.

(ix) Infectious Diseases.

Compounds, compositions and methods of the invention are useful in PDT to treat infectious diseases. For example, Cutaneous leishmaniasis and subcutaneous leishmaniasis, which occurs extensively in the Mediterranean and Mideast regions, is currently treated with arsenic-containing compounds. PDT has been used to reasonable effect recently, at least in one case, on a human patient. The use of compounds and compositions of the present invention are likewise useful, and potentially offer advantages such as ease of synthesis and better spectral absorption properties.

(x) Tissue Sealants.

Compounds, compositions and methods of the invention are useful in PDT as tissue sealants in subjects in need thereof. Light-activated tissue sealants are attractive for sealing wounds, bonding tissue, and closing defects in tissue There are many applications where sutures or staples are undesirable, and use of such mechanical methods of sealing often lead to infection and scarring.

(xi) Neoplastic Disease.

Compounds, compositions and methods of the invention are useful in PDT for treating neoplastic diseases or cancers, including skin cancer, lung cancer, colon cancer, breast cancer, prostate cancer, cervical cancer, ovarian cancer, basal cell carcinoma, leukemia, lymphoma, squamous cell carcinoma, melanoma, plaque-stage cutaneous T-cell lymphoma, and Kaposi sarcoma.

B. Imaging Enhancing Agents.

In addition to PDT, the compositions provided herein can be used as imaging enhancing agents in diagnostic imaging techniques, or for the labeling of target tissues or target compositions for diagnostic radiology. In the modern medical field, there are a variety of treatments including magnetic resonance imaging (MRI) for the diagnosis of diseases. Detection of cancer in its early stages should improve the ability to cure eliminate the cancerous tissue. Early diagnosis of precancerous regions and minute cancer are important subject matters in modern cancer treatments. MRI has emerged as a powerful tool in clinical settings because it is noninvasive and yields an accurate volume rendering of the subject. The image is created by imposing one or more orthogonal magnetic field gradients upon the subject or specimen while exciting nuclear spins with radio frequency pulses as in a typical nuclear magnetic resonance (NMR) experiment. After collection of data with a variety of gradient fields, deconvolusion yields a one, two, or three dimensional image of the specimen/subject. Typically, the image is based on the NMR signal from the protons of water where the signal intensity in a given volume element is a function of the water concentration and relaxation times. Local variation in there parameters provide the vivid contrast observed in MR images.

MRI contrast agents act by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American 246: 78 (1982); Runge et al., Am. J. Radiol. 141: 1209 (1983). When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI image enhancing agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues (U.S. Pat. No. 5,059,415). Unfortunately, the relaxivity of Gd bound to antibodies has been found to be only slightly better than that of unbound Gd-DTPA (Paajanen et al., Magn. Reson. Med 13: 38-43 (1990)).

MRI is generally used to detect $^1H$ nuclei in the living body. However, MRI is capable of detecting NMR spectrums of other nuclear species, including $^{13}C$, $^{15}N$, $^{31}P$, and $^{19}F$. The $^{19}F$ is not abundant in the living body. By incorporating isotopes useful in MRI, such as $^{13}C$, $^{15}N$, $^{31}P$, or $^{19}F$, and particularly $^{19}F$ in the compositions provided herein and administering to a subject, the compounds provided herein would accumulate in target tissue, and subsequent MR imaging would produce NMR data with enhanced signal from the targeted tissue or target compositions due to the presence of the accumulated compound with the MRI recognizable isotope, such as $^{19}F$. Thus, the disclosed compounds can be used as image enhancing agents and provide labeling of specific target tissues or target compositions for diagnostic radiology, including MRI.

C. Detecting Target Tissue or Target Compositions.

In addition to PDT, the compositions provided herein can be used to detect target cells, target tissue, or target compositions in a subject. When the compounds provided herein are to be used for detection of target tissue or target composition, the compounds are introduced into the subject and sufficient time is allowed for the compounds to accumulate in the target tissue or to become associated with the target composition. The area of treatment is then irradiated, generally using light of an energy sufficient to cause fluorescence of the compound, and the energy used is usually significantly lower than is required for photodynamic therapy treatment. Fluorescence is determined upon exposure to light at the desired wavelength, and the amount of fluorescence can be correlated to the presence of the compound, qualitatively or quantitatively, by methods known in the art.

D. Diagnosing an Infecting Agent.

The compositions provided herein can be used to diagnose the presence of an infecting agent, or the identity of an infecting agent in a subject. The compounds provided herein can be conjugated to one or more ligands specific for an infecting agent, such as an antibody or antibody fragment, that selectively associates with the infecting agent, and after allowing sufficient time for the targeted compound to associate with the infecting agent and to clear from non-target tissue, the compound can be visualized, such as by exposing to light of an energy sufficient to cause fluorescence of the compound, or by imaging using diagnostic radiology, including MRI. By way of example, any one of the compounds provided herein can be conjugated to an antibody that is targeted against a suitable *Helicobacter pylori* antigen, and formulated into a pharmaceutical preparation that, when introduced into a subject, releases the conjugated compound to a gastric mucus/epithelial layer where the bacterium is found. After sufficient time for the compound to selectively associate with the target infecting agent, and for any unbound compound to clear from non-target tissue, the subject can be examined to determine whether any *Helicobacter pylori* is present. This can be done by MRI to detect accumulated compound because of the presence of $^{19}$F substituents, for example, or by irradiating the suspect target area with light of an energy sufficient to cause fluorescence of the compound, such as by using fiberoptics, and detecting any fluorescence of the targeted compound.

3. Solar Cells, Light Harvesting Rods and Light Harvesting Arrays.

Bacteriochlorins of Formula I herein may be used as chromophores (also referred to as photosensitizers or simply sensitizers) in solar cells, including but not limited to high surface area colloidal semiconductor film solar cells (Gratzel cells), as described in, for example, U.S. Pat. Nos. 5,441,827; 6,420,648; 6,933,436; 6,924,427; 6,913,713; 6,900,382; 6,858,158; and 6,706,963.

Bacteriochlorins of Formula I may be used as chromophores in the light harvesting rods described in U.S. Pat. Nos. 6,407,330 and 6,420,648 (incorporated herein by reference). The light harvesting rod may comprise one or more bacteriochlorins of Formula I coupled to one or two adjacent chromophores depending upon the position thereof in the light harvesting rod. Such light harvesting rods may be utilized to produce light harvesting arrays as described in U.S. Pat. No. 6,420,648 and solar cells as described in U.S. Pat. No. 6,407,330.

4. Flow Cytometry.

Flow cytometry is known and described in, for example, U.S. Pat. Nos. 5,167; 5,915,925; 6,248,590; 6,589,792; and 6,890,487. In some embodiments the particle being detected, such as a cell, is labelled with a luminescent compound such as a phosphor or fluorophore for detection. Labelling can be carried out by any suitable technique such as coupling the luminescent compound to another compound such as an antibody which in turn specifically binds to the particle or cell, by uptake or internalization of the luminescent compound into the cell or particle, by non-specific adsorption of the luminescent compound to the cell or particle, etc. The bacteriochlorins described herein are useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

5. Information Storage Devices.

Bacteriochlorins of the invention are also useful immobilized to a substrate for making charge storage molecules and information storage devices containing the same, either individually or as linked polymers thereof, either optionally including additional compounds to add additional oxidation states. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The bacteriochlorins of the invention may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the following non-limiting Examples.

EXPERIMENTAL

To achieve a trans-AB substituent pattern in bacteriochlorins, we considered that alternative dihydrodipyrrin units could be employed in the self-condensation. Because the acetal carbon of the dihydrodipyrrin-acetal (i.e., the α-carbon at the 1-position) forms the 5- and 15-carbons of the bacteriochlorin, alternative substituents at the "acetal" α-carbon could be conveyed in lieu of the methoxy group to the bacteriochlorin 5-position. The 15-position would then be accessible for bromination and subsequent substitution processes. This analysis is consistent with our current conceptualization of the mechanism of formation of the 5-methoxybacteriochlorin as is shown in Scheme 2. Treatment of the dihydrodipyrrin-acetal with TMSOTf affords an oxocarbenium ion and eliminates one molecule of methanol (as the trimethylsilyl ether); the oxocarbenium ion serves as the electrophile for attack by pyrrole of the other dihydrodipyrrin-acetal. Repetition of this process eliminates a second molecule of methanol and affords the 5,15-dimethoxy-5,15-dihydrobacteriochlorin. Elimination of the third molecule of methanol results in the aromatic bacteriochlorin macrocycle containing the 5-methoxy substituent.[25]

Scheme 2. Key Steps in the Formation of 5-Methoxybacteriochlorin

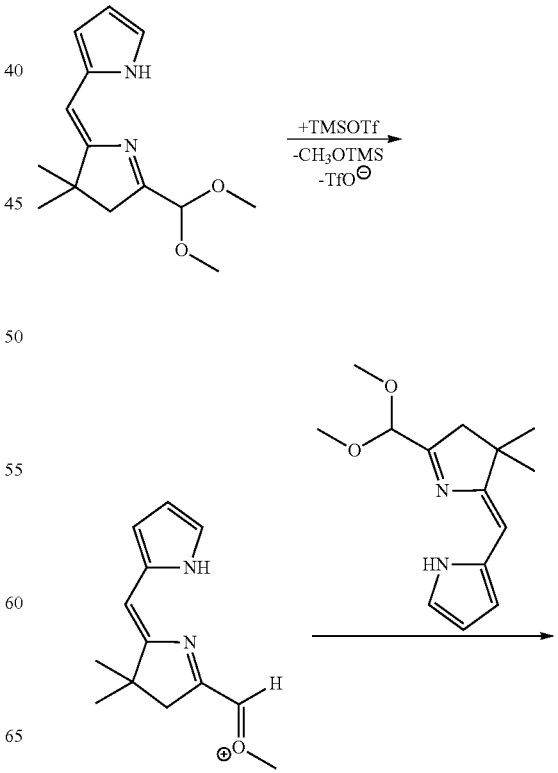

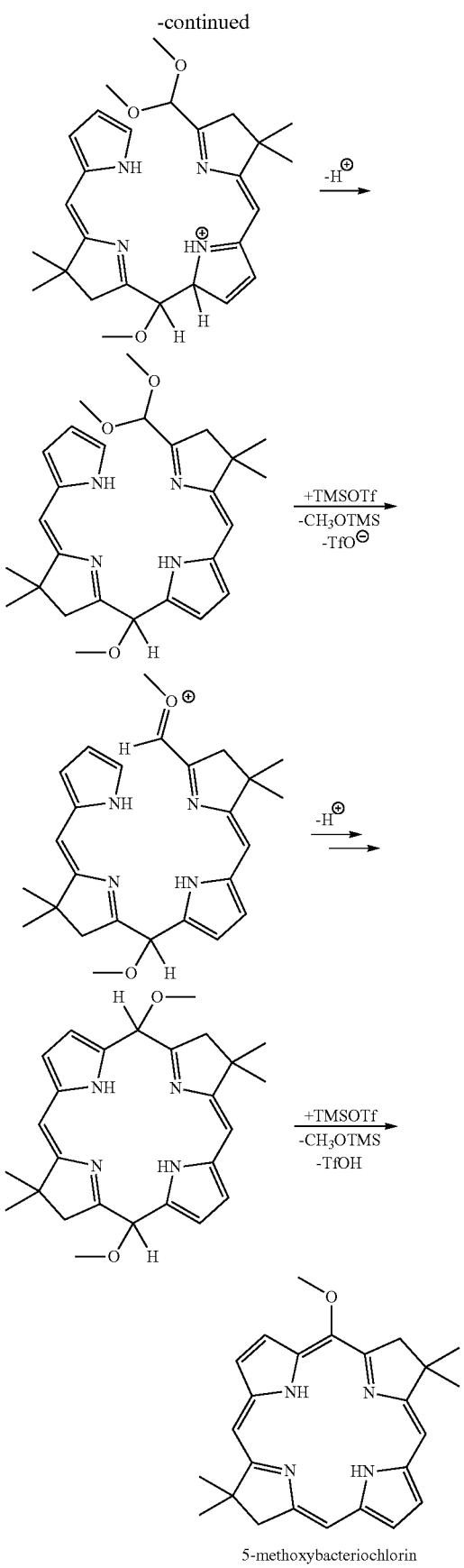

5-methoxybacteriochlorin

We herein report the synthesis of a handful of dihydrodipyrrins (containing diverse substituents at the 1-position) and investigate their conversion to bacteriochlorins. The synthesis of the dihydrodipyrrins was facilitated by the development of a new route to the α,β-unsaturated ketone-acetal 1a (the Michael acceptor in formation of the dihydrodipyrrin-acetal), which also is reported herein. The reactivity of four new dihydrodipyrrins toward bacteriochlorin formation was examined. In so doing, one new bacteriochlorin was obtained, which contains a 5-(2-hydroxyethoxy) substituent. Bromination of the 5-(2-hydroxyethoxy)bacteriochlorin proceeded smoothly at the 15-position, affording the bacteriochlorin with reactive functional groups in a trans-AB architecture. In total, the study has afforded a deeper understanding of the structural features of the hydrodipyrrin for successful self-condensation, and has opened a new pathway for introducing substituents into the bacteriochlorin macrocycle.

RESULTS AND DISCUSSION

I. Synthesis of Michael Acceptors.
1. Dimethoxymethyl α,β-Unsaturated Ketone 1a
A. Reconnaisance.

The first reported synthesis of Michael acceptor 1a was carried out in 56% yield when 2 mmol of mesityl oxide was treated with a stoichiometric amount of diphenyl diselenide and excess ammonium peroxydisulfate in methanol (Scheme 3).[34] A subsequent scaled-up procedure employed a catalytic amount of diphenyl diselenide and afforded 1a in 29% yield,[25] yet significant drawbacks to the synthesis of 1a remain as follows: (i) use of expensive and toxic diphenyl diselenide; (ii) difficult purification including distillation followed by extensive chromatography, and (iii) relatively low yield. Moreover, the method has limited scope for introduction of substituents other than the dimethoxymethyl unit, which gives rise to the 5-methoxy substituent in the bacteriochlorin. Here, a scalable and more versatile synthesis of Michael acceptors was developed. The synthesis was envisaged to entail reaction of 2-methyl-1-propenylmagnesium bromide with an acetal-containing nitrile or N-methoxy-N-methylamide (Scheme 3).

Scheme 3. Prior and Envisaged Routes to Michael Acceptors

Prior synthesis

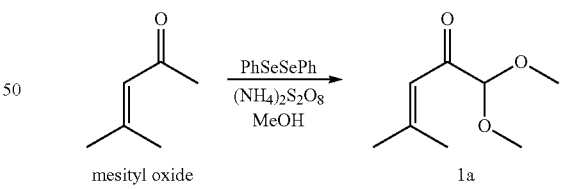

mesityl oxide        1a

New synthetic approach

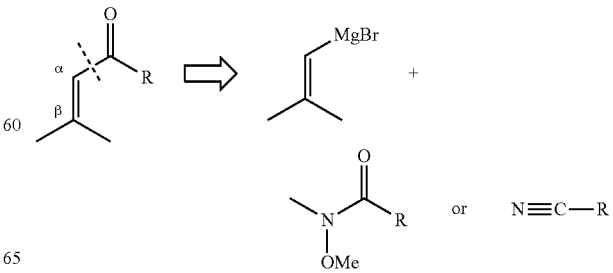

B. New Synthesis of Ketone 1a.

In our initial studies we attempted to convert methyl dimethoxyacetate (4) to dimethoxymethyl ketone 1a via treatment of the N-methoxy-N-methylamide (Weinreb amide) intermediate with an organomagnesium reagent.[35] The Weinreb amide is prepared by treatment of an ester with i-PrMgCl and Me(MeO)NH.HCl.[36] However, when the slurry of 4 and 1.25 molar equiv of N,O-dimethylhydroxylamine hydrochloride in THF was treated with 2.5 molar equiv of i-PrMgCl at −20° C. according to a general procedure,[36] putative isopropylketone A and unreacted ester 4 were obtained in 1:1 ratio (Scheme 4). Reversal of the order of addition (treatment of i-PrMgCl with Me(MeO)NH.HCl at −25° C. for 40 min followed by 4)[37] gave the same result. On the other hand, the attempted direct conversion by treatment of 4 and Me(MeO)NH.HCl with 3.3 molar equiv of 2-methyl-1-propenylmagnesium bromide at −20° C. afforded an inseparable mixture that contained the desired 1a and a putative tertiary alcohol (B) in 3:5 ratio as determined by GC-MS and $^1$H NMR analysis.

Scheme 4. Attempted Synthesis for the Dimethoxymethyl-Containing Michael Acceptor 1a

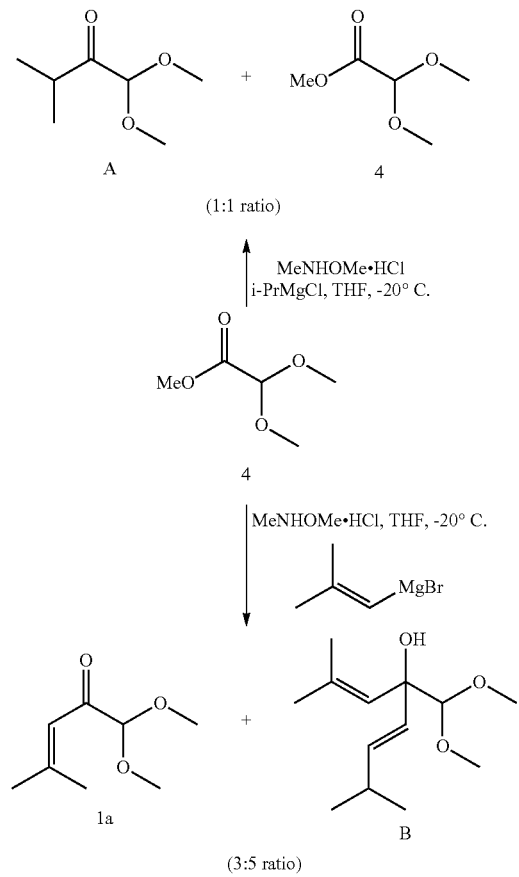

An alternative synthesis is shown in Scheme 5. Treatment of trimethyl orthoformate with an equimolar amount of trimethylsilyl cyanide in the presence of 10 mol % of BF$_3$.OEt$_2$ afforded dimethoxyacetonitrile (5).[38,39] Reaction of the latter with 1.2 molar equiv of 2-methyl-1-propenylmagnesium bromide at room temperature for 2.5 h followed by hydrolysis with saturated aqueous NH$_4$Cl afforded 1a as the major product. The 2-step synthesis was carried out at 185-mmol scale with streamlined workup procedures: distillation at atmospheric pressure gave 5 in 90% yield (8-fold larger than the literature procedure[38]), and distillation at reduced pressure gave 1a in 57% yield (16.5 g, 90% purity). The 2-step synthesis of 1a also uses little solvent. The conversion of trimethyl orthoformate to 5 is solvent-free, and the conversion of 5 to 1a employs 2-methyl-1-propenylmagnesium bromide, which is available commercially as a 0.5 M solution in THF. No other solvent is employed. In this regard, both reactions are carried out at the highest possible concentration, an approach commensurate with the objective of preparing multigram quantities of the valuable intermediate 1a.

Scheme 5. Scalable Synthesis of Michael Acceptor 1a

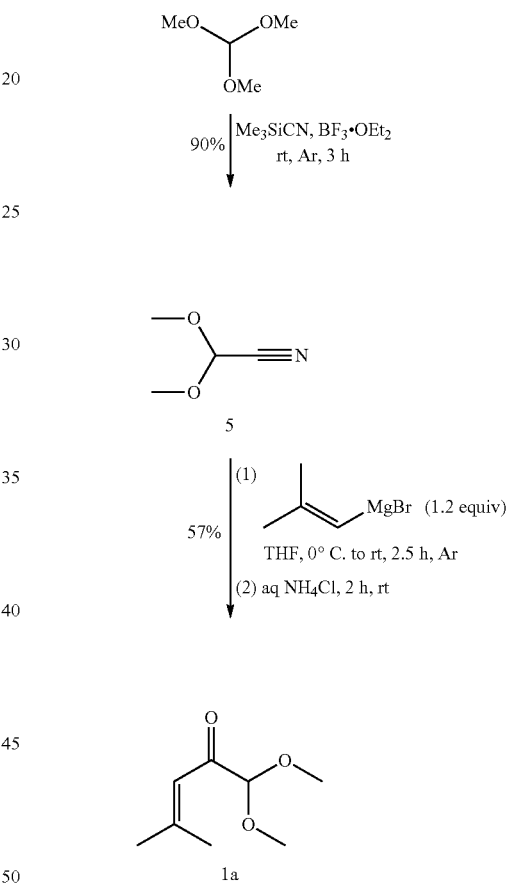

2. Synthesis of Michael Acceptors Containing Cyclic Acetal Units.

The new route to Michael acceptors enabled expansion of the structural diversity of these intermediates. Diethoxymethyl Michael acceptor 1b was prepared from commercially available diethoxyacetonitrile in analogy with the synthesis of 1a. Transacetalization of diethoxyacetal 1b with 1,3-propanediol in benzene/TsOH afforded 1,3-dioxane 1c in 64% yield. On the other hand, attempted transacetalization of 1b with ethylene glycol gave an inseparable mixture consisting of 1,3-dioxolane 1d and a by-product assumed to be bis(1,3-dioxolane) C (Scheme 6). Transacetalization of diethoxyacetonitrile with ethylene glycol in the presence of TsOH also did not proceed. Therefore, we considered an alternative approach to 1d.

Scheme 6. Synthesis and Transacetalization of a Diethoxymethyl-Containing Michael Acceptor

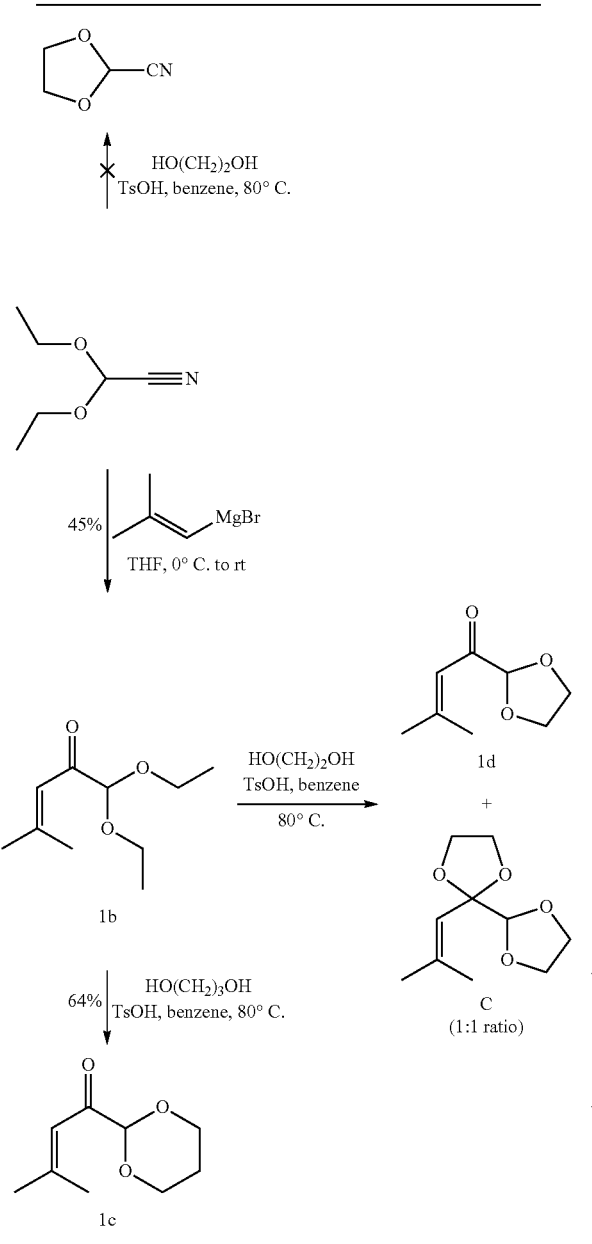

Scheme 7. Synthesis of a 1,3-Dioxolane-Containing Michael Acceptor

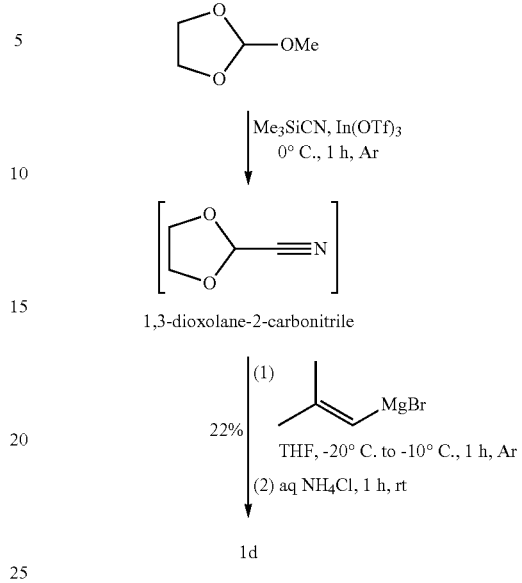

3. Synthesis of Phenoxymethyl and Methoxymethyl-Containing Michael Acceptors. Methoxymethyl Michael acceptor 1e was obtained in 22% yield when α-methoxyacetic acid (6e) was treated with 1,1'-carbonyldiimidazole (CDI) and N,O-dimethylhydroxylamine hydrochloride followed by 2-methyl-1-propenylmagnesium bromide (Scheme 8). The reaction of known phenoxymethyl Weinreb amide 7f (prepared from phenoxyacetic acid (6f) and N,O-dimethylhydroxylamine hydrochloride with CDI)[41] with 1.3 molar equiv of 2-methyl-1-propenylmagnesium bromide afforded phenoxymethyl Michael acceptor 1f in quantitative yield. Similarly, treatment of α-methoxyphenylacetic acid (6g) with CDI followed by triethylamine and N,O-dimethylhydroxylamine hydrochloride afforded amide 7g in 58% yield. (The S-enantiomer of 7g is described in the literature, but without characterization data or experimental procedure.[42]) The reaction of 7g with 1.1 molar equiv of 2-methyl-1-propenylmagnesium bromide afforded α-methoxybenzyl Michael acceptor 1g in 87% yield.

Treatment of 2-methoxy-1,3-dioxolane with 1 molar equiv of trimethylsilyl cyanide in the presence of a catalytic amount of In(OTf)$_3$ for 1 h at 0° C. afforded 1,3-dioxolane-2-carbonitrile. (An exploratory survey showed BF$_3$·OEt$_2$, InCl$_3$ and Yb(OTf)$_3$ to give additional by-products as observed upon $^1$H NMR analysis of crude samples.) The $^1$H NMR spectrum of the crude 1,3-dioxolane-2-carbonitrile was consistent with literature data,[40] although methods for the synthesis of this compound have not been reported. The dioxolane-nitrile was found to be unstable, and for this reason was used directly in the next step. Treatment of the crude nitrile with 2-methyl-1-propenylmagnesium bromide afforded 1d in 22% overall yield (Scheme 7). Compound 1d was found to be very unstable in air, but could be stored at –20° C. for several months without decomposition in a degassed ether solution.

Scheme 8. Synthesis of Methoxymethyl and Phenoxymethyl-Containing Michael Acceptors

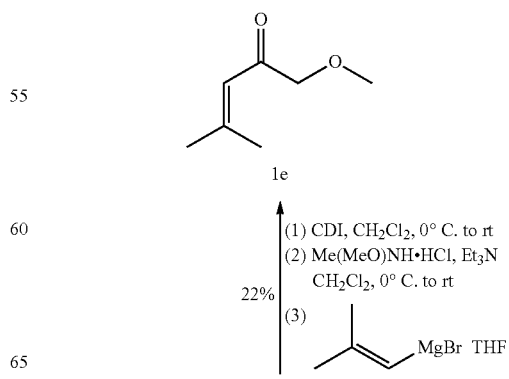

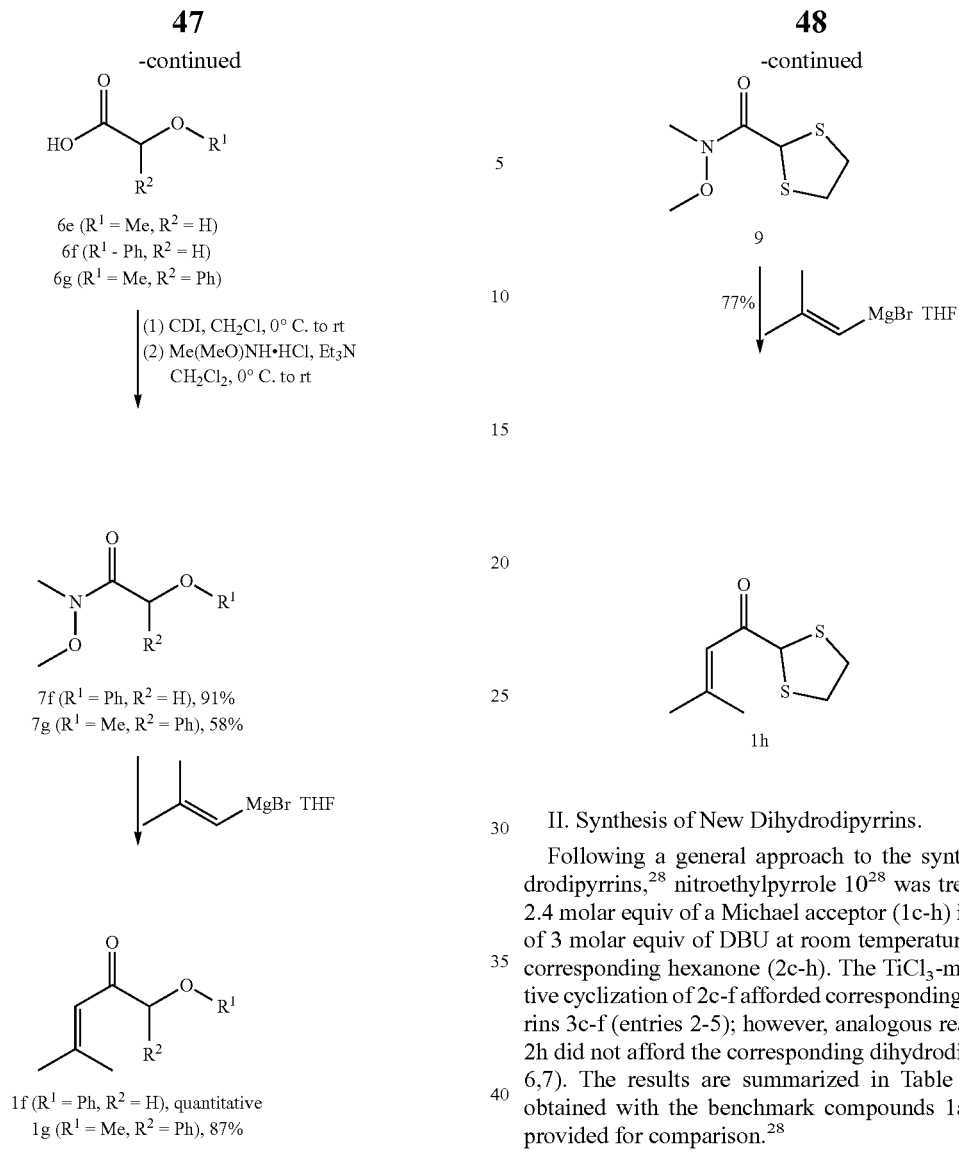

II. Synthesis of New Dihydrodipyrrins.

Following a general approach to the synthesis of dihydrodipyrrins,[28] nitroethylpyrrole 10[28] was treated with 1.1-2.4 molar equiv of a Michael acceptor (1c-h) in the presence of 3 molar equiv of DBU at room temperature to afford the corresponding hexanone (2c-h). The $TiCl_3$-mediated reductive cyclization of 2c-f afforded corresponding dihydrodipyrrins 3c-f (entries 2-5); however, analogous reaction of 2g or 2h did not afford the corresponding dihydrodipyrrin (entries 6,7). The results are summarized in Table 1. The yields obtained with the benchmark compounds 1a→2a→3a are provided for comparison.[28]

4. Synthesis of 1,3-Dithiolane-Containing Michael Acceptor. Treatment of a slurry of ethyl 1,3-dithiolane-2-carboxylate (8) and 2.50 molar equiv of N,O-dimethylhydroxylamine hydrochloride in THF with 5 molar equiv of isopropylmagnesium chloride at −78° C. afforded 9 in 49% yield. Compound 9 was prepared previously via a different method.[43] The reaction of Weinreb amide 9 with 1.1 molar equiv of 2-methyl-1-propenylmagnesium bromide afforded Michael acceptor 1h in 77% yield (Scheme 9).

Scheme 9. Synthesis of a 1,3-Dithiolane-Containing Michael Acceptor

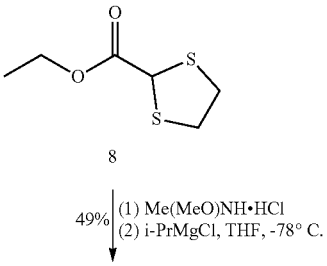

TABLE 1

Synthesis of Dihydrodipyrrins Containing Diverse 1-Substituents

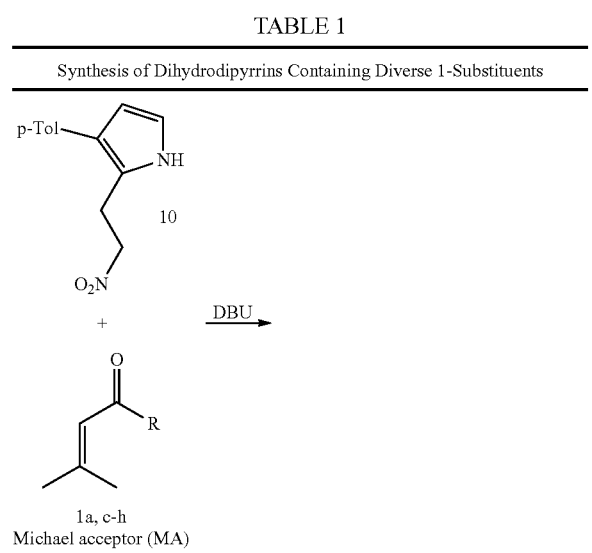

TABLE 1-continued

Synthesis of Dihydrodipyrrins Containing Diverse 1-Substituents

Reaction scheme: Hexanone (2a, c-h) with p-Tol-pyrrole-NH, -NO2, gem-dimethyl, and O=R ketone group → (1) NaOMe/THF (2) TiCl$_3$, pH 6 → Dihydrodipyrrin (DHDP) 3a, c-f (p-Tol-pyrrole-NH connected via =CH to pyrrolinyl with gem-dimethyl and R substituent)

| Entry | MA | R | Hexanone | Yield, % | DHDP | Yield, % |
|---|---|---|---|---|---|---|
| 1[28] | 1a | –CH(OMe)(OMe) (dimethoxymethyl) | 2a | 63 | 3a | 54 |
| 2 | 1c | 1,3-dioxan-2-yl | 2c | 35 | 3c | 18 |
| 3 | 1d | 1,3-dioxolan-2-yl | 2d | 54 | 3d | 31 |
| 4 | 1e | –CH$_2$OMe (methoxymethyl) | 2e | 70 | 3e | 22 |
| 5 | 1f | –CH$_2$OPh (phenoxymethyl) | 2f | 60 | 3f | 37 |
| 6 | 1g | –CH(OMe)(Ph) | 2g | 63 | 3g | 0 |
| 7 | 1h | 1,3-dithiolan-2-yl | 2h | 36 | 3h | 0 |

III. Self-Condensation Study.

The self-condensation conditions (5 equiv of TMSOTf and 20 equiv of 2,6-DTBP in CH$_2$Cl$_2$) employed previously for dihydrodipyrrin-acetals bearing a 1-(dimethoxymethyl) unit and diverse β-pyrrole substituents[28] were recently modified to use a lesser amount of reagents (4 equiv of TMSOTf and 8 equiv of 2,6-DTBP).[46] The latter conditions were applied with hydrodipyrrins 3c-f. The results are shown in Table 2. For comparison, dihydrodipyrrin-acetal 3a affords bacteriochlorin BC-1 (entry 1). Dihydrodipyrrin-dioxane 3c resulted in partial decomposition and no bacteriochlorin (entry 2), whereas dihydrodipyrrin-dioxolane 3d successfully afforded a bacteriochlorin (entry 3; vide infra). Dihydrodipyrrin 3e, bearing a methoxymethyl group, gave only a small LD-MS peak corresponding to a tetradehydrocorrin[25,47] macrocycle, but the product was not isolated (entry 4). Dihydrodipyrrin 3f, bearing a phenoxymethyl group, gave decomposition with no starting material or macrocycle observed (entry 5).

TABLE 2

Self-Condensation Survey of Dihydrodipyrrins

Reaction: Dihydrodipyrrin 3a, c-f (structure with p-tolyl group on pyrrole, connected via =CH to pyrrolinyl bearing gem-dimethyl and R substituent) → TMSOTf (4 equiv), 2,6-DTBP (8 equiv), CH$_2$Cl$_2$, rt, overnight, 18 mM → Bacteriochlorin?

| Entry | R | Dihydrodipyrrin | Result |
|---|---|---|---|
| 1 | –CH(OMe)(OMe) | 3a | BC-1 |
| 2 | 1,3-dioxan-2-yl | 3c | Unreacted 3c + decomposition |
| 3 | 1,3-dioxolan-2-yl | 3d | BC-3 |
| 4 | –CH$_2$OMe | 3e | Unreacted 3e, trace TDC$^a$ + decomposition |
| 5 | –CH$_2$OPh | 3f | decomposition |

$^a$TDC is a tetradehydrocorrin species.

The successful reaction of dihydrodipyrrin 3d in the survey reaction prompted scale-up to fully characterize the resulting bacteriochlorin. Thus, the self-condensation of dihydrodipyrrin 3d (0.76 mmol) in the presence of 4 molar equiv of TMSOTf and 8 molar equiv of 2,6-DTBP in CH$_2$Cl$_2$ afforded bacteriochlorin BC-3 in 30% yield; no other macrocycles were observed by TLC and LD-MS analyses. Consistent with the mechanistic picture shown in Scheme 2, bacteriochlorin BC-3 contained a 2-(trimethylsilyloxy)ethoxy group at the 5-position (Scheme 10). Treatment with 1.5 molar equiv of TBAF at room temperature under argon cleaved the TMS group and afforded the 5-(2-hydroxyethoxy)bacteriochlorin BC-4 in 83% yield.

Scheme 10. Synthesis of a trans-AB-Bacteriochlorin

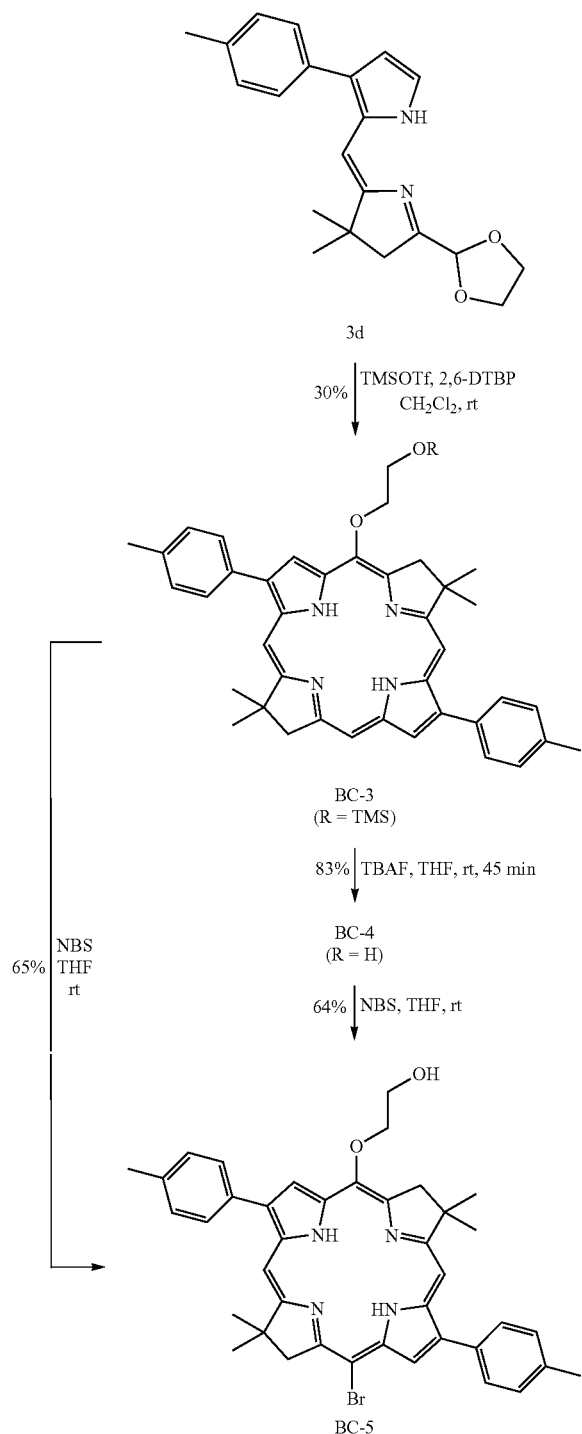

when TMS-protected bacteriochlorin BC-3 was treated with 1 molar equiv of NBS, bacteriochlorin BC-5 was obtained as well in 65% yield indicating that NBS acted both as a deprotecting and brominating agent. Bacteriochlorin BC-5 contains two reactive functional groups at opposing meso positions. Analogues of BC-5 that bear diverse β-pyrrole substituents and the same trans-AB substituents are expected to afford valuable building blocks.

Outlook.

The new route to Michael acceptor 1a has enabled the synthesis of a number of analogues with diverse substituents in place of the dimethoxymethyl unit: 1,3-dioxolan-2-yl, 1,3-dithiolan-2-yl, 1,3-dioxan-2-yl, methoxymethyl-, phenoxymethyl- and α-methoxybenzyl. Upon screening four new dihydrodipyrrins with distinct electrophilic centers, a dihydrodipyrrin bearing a 1,3-dioxolan-2-yl group (3d) was found to afford the corresponding 5-(2-hydroxyethoxy)bacteriochlorin (BC-4). Consistent with the mechanism of 5-methoxybacteriochlorin formation, the condensation of two molecules of a dihydrodipyrrin bearing a 1,3-dioxolan-2-yl group is accompanied by formal release of three alcohol units as well, but the third moiety is an integral part of the hydroxyethoxy unit anchored at the 5-position of the bacteriochlorin. Previously, the only type of 1-substituent in a dihydrodipyrrin that afforded a bacteriochlorin was a dimethoxymethyl unit (e.g., 3a).[25,28] Although a singular success from a broad survey, the resulting bacteriochlorin BC-4 and its 15-brominated derivative (BC-5) are expected to be valuable building blocks given the orthogonality and linear arrangement of the functional groups disposed at the 5- and 15-positions.

Experimental Section

General Methods.

$^1$H NMR (300 MHz) and $^{13}$C NMR (100 MHz) spectra were collected at room temperature in CDCl$_3$ unless noted otherwise. Absorption spectra were obtained in toluene at room temperature unless noted otherwise. Electrospray ionization mass spectrometry (ESI-MS) data are reported for the molecular ion or protonated molecular ion. Bromination of bacteriochlorins was performed using freshly recrystallized NBS (from water). THF used in all reactions was freshly distilled from Na/benzophenone ketyl. The purity of noncommercial compounds prepared by literature procedures was determined by $^1$H NMR spectroscopy. All commercially available materials (including reactants 4, 6e-g and 8) were used as received. Non-commercially available compounds 10 and 11 were prepared as described in the literature.[28]

1,1-Dimethoxy-4-methyl-3-penten-2-one (1a)

Dimethoxyacetonitrile (5, 18.7 g, 185 mmol) in a 1-L round bottom flask equipped with a stirring bar and a 500-mL addition funnel (all oven-dried) was treated under argon with 2-methyl-1-propenylmagnesium bromide (445 mL, 222 mmol, 0.5 M in THF) over 30 min at 0° C. After the addition was completed, the reaction mixture was stirred for 2 h at room temperature, affording a bright yellow-orange solution. Saturated aqueous NH$_4$Cl (500 mL) was added, and the reaction mixture was vigorously stirred at room temperature for 2 h. The completion of hydrolysis was monitored by $^1$H NMR spectroscopy (disappearance of peaks at 5.89 ppm and 4.61 ppm (imine) and appearance of peaks at 6.34 ppm and 4.49 ppm). The aqueous phase was extracted with Et$_2$O (3×350 mL), and each organic extract was washed (brine). The combined organic extract was dried (Na$_2$SO$_4$) and concentrated to an orange liquid. Bulb-to-bulb distillation (95° C./0.05 mmHg) afforded a yellow liquid (16.5 g, 57%, 90% purity).

Bacteriochlorins with a 5-methoxy group undergo smooth and selective bromination at the 15-position, whereas bacteriochlorins lacking a 5-methoxy group typically afford a mixture of bromobacteriochlorins.[28,33] To examine whether the hydroxyethoxy group directed selective bromination, bacteriochlorin BC-4 was treated with 1 molar equiv of NBS at room temperature. The resulting bacteriochlorin (BC-5) was obtained in 64% yield and contained a bromine atom at the 15-position (established by NOESY). On the other hand, The characterization values ($^1$H NMR) were consistent with those in the literature.[25,34] IR (neat) 3518, 2937, 2834, 1699, 1620, 1445, 1381, 1192, 1106, 1073, 988, 846 cm$^{-1}$.

Attempted Formation of the Weinreb Amide Intermediate for the Synthesis of 1,1-Dimethoxy-4-methyl-3-penten-2-one (1a).

(A) According to a general procedure for formation of a Weinreb intermediate,[36] a vigorously stirred slurry of methyl dimethoxyacetate (4, 200 µL, 1.64 mmol) and N,O-dimethylhydroxylamine hydrochloride (201 mg, 2.05 mmol) in THF (2.4 mL) under argon was treated dropwise with isopropylmagnesium bromide (2.05 mL, 4.10 mmol, 2 M solution in THF) at −20° C. The resulting heterogeneous reaction mixture was stirred for 1.5 h at −20° C. under argon. The reaction mixture was quenched with saturated aqueous NH$_4$Cl and H$_2$O (1:1). After extraction with ether (3×50 mL), the combined organic extract was washed (brine), dried (Na$_2$SO$_4$) and concentrated under vacuum at room temperature. The $^1$H NMR spectrum of the crude product showed unreacted 4 and signals consistent with those reported for 1,1-dimethoxy-3-methylbutan-2-one (A).[34]

(B) According to a general procedure for formation of a Weinreb intermediate with reversed order of addition,[37] a slurry of isopropylmagnesium bromide (3.28 mL, 6.56 mmol, 2 M in THF) and N,O-dimethylhydroxylamine hydrochloride (321 mg, 3.28 mmol) in THF (6.6 mL) under argon was stirred for 40 min at −25° C. Methyl dimethoxyacetate (4, 200 µL, 1.64 mmol) was added, and the reaction mixture was stirred for 45 min at −25° C. under argon. The reaction mixture was quenched with saturated aqueous NH$_4$Cl and H$_2$O (1:1). After extraction with ether (3×50 mL), the combined organic extract was washed (brine), dried (Na$_2$SO$_4$) and concentrated under vacuum at room temperature. The $^1$H NMR spectrum of the crude product showed unreacted 4 and signals consistent with those reported for 1,1-dimethoxy-3-methylbutan-2-one (A).[34]

Attempted Synthesis of 1,1-Dimethoxy-4-methyl-3-penten-2-one (1a) Via In Situ Formation and Reaction of the Weinreb Amide Intermediate.

A vigorously stirred solution of 4 (200 µL, 1.64 mmol) and N,O-dimethylhydroxylamine hydrochloride (193 mg, 1.97 mmol) under argon was treated with 2-methyl-1-propenylmagnesium bromide (10.8 mL, 5.40 mmol, 0.5 M in THF) dropwise over 45 min at −20° C. The reaction mixture was stirred for 1 h at −20° C. Saturated aqueous NH$_4$Cl and water (1:1) were added. The aqueous phase was extracted with ether (3×50 mL) The combined organic extract was washed (brine), dried (Na$_2$SO$_4$) and concentrated leaving a yellow liquid. The $^1$H NMR spectrum of the major product isolated by column chromatography [silica, hexanes/EtOAc (5:1)] showed a mixture of the desired product and a by-product (a putative tertiary alcohol, B) in a 3:5 ratio.

1,1-Diethoxy-4-methyl-3-penten-2-one (1b)

Diethoxyacetonitrile (5.00 g, 38.8 mmol) in a 250-mL round bottom flask equipped with a stirring bar and an addition funnel (all oven-dried) was treated under argon with 2-methyl-1-propenylmagnesium bromide (93 mL, 46.5 mmol, 0.5 M in THF) over 30 min at room temperature under argon. After the addition was completed, the reaction mixture was stirred for 1 h at room temperature, affording a bright yellow-orange solution. Saturated aqueous NH$_4$Cl (350 mL) was added, and the reaction mixture was transferred into a beaker and vigorously stirred at room temperature for 2.5 h. The completion of hydrolysis was monitored by $^1$H NMR spectroscopy (disappearance of peaks at 5.93 ppm and 4.73 ppm (imine) and appearance of peaks at 6.40 ppm and 4.58 ppm). The aqueous phase was extracted with Et$_2$O (3×200 mL). The combined organic extract was washed (brine), dried (Na$_2$SO$_4$) and concentrated to an orange liquid, which was chromatographed [silica, EtOAc/hexanes (1:9)] to afford a yellow liquid (3.27 g, 45%): $^1$H NMR δ 1.25 (t, J=7.4 Hz, 6H), 1.95 (s, 3H), 2.20 (s, 3H), 3.52-3.74 (m, 4H), 4.58 (s, 1H), 6.40 (s, 1H); $^{13}$C NMR δ 15.4, 21.5, 28.4, 63.2, 103.3, 119.2, 160.1, 194.9; ESI-MS obsd 209.1148, calcd 209.1148 [(M+Na)$^+$, M=C$_{10}$H$_{18}$O$_3$]; IR (neat) 2976, 2880, 1697, 1620, 1444, 1380, 1317, 1235, 1104, 1060, 986, 845 cm$^{-1}$.

1-(1,3-Dioxan-2-yl)-3-methyl-2-buten-1-one (1c)

A solution of 1b (1.02 g, 5.49 mmol) and 1,3-propanediol (0.600 mL, 8.23 mmol) in benzene (10.8 mL) was treated with p-toluenesulfonic acid (522 mg, 2.75 mmol). The reaction mixture was stirred at 80° C. for 4.5 h. Saturated aqueous NaHCO$_3$ was added, and the mixture was extracted with Et$_2$O. The organic extract was washed (water), dried (Na$_2$SO$_4$), concentrated to a brown liquid, and chromatographed [silica, hexanes/EtOAc (5:1)] to afford a yellow liquid (600 mg, 64%): $^1$H NMR δ 1.40-1.45 (m, 1H), 1.96 (s, 3H), 2.20 (s, 3H), 2.12-2.25 (m, 1H), 3.83-3.92 (m, 2H), 4.20-4.26 (m, 2H), 4.79 (s, 1H), 6.42 (s, 1H); $^{13}$C NMR δ 21.7, 25.9, 28.5, 67.3, 101.4, 119.0, 161.2, 192.1; ESI-MS obsd 193.0833, calcd 193.0835 [(M+Na)$^+$, M=C$_9$H$_{14}$O$_3$].

1-(1,3-Dioxolan-2-yl)-3-methyl-2-buten-1-one (1d)

A solution of 2-methoxy-1,3-dioxolane (5.00 mL, 53.7 mmol) and trimethylsilyl cyanide (7.16 mL, 53.7 mmol) in CH$_2$Cl$_2$ (107.4 mL) at 0° C. was treated under argon with In(OTf)$_3$ (377 mg, 0.671 mmol). After stirring for 1 h at 0° C., the reaction mixture was quenched with saturated aqueous NaHCO$_3$. After extraction, the organic phase was washed (water), dried (Na$_2$SO$_4$) and concentrated. The characterization values ($^1$H NMR and $^{13}$C NMR) of the crude 1,3-dioxolane-2-carbonitrile were consistent with values reported in the literature.[40] A solution of the crude 1,3-dioxolane-2-carbonitrile in THF (10 mL) in a two-neck round bottom flask equipped with an addition funnel was bubbled with argon for 10 min, upon which the flask contents were treated dropwise with 2-methyl-1-propenylmagnesium bromide (107.4 mL, 53.7 mmol, 0.5 M in THF) at −20° C. under argon. The reaction mixture was stirred for 1 h at −10° C. and bubbled with argon. Saturated aqueous NH$_4$Cl (150 mL) was added, and the reaction mixture was stirred vigorously for 1 h at room temperature. The reaction mixture was extracted with Et$_2$O (3×150 mL). The combined organic extract was washed (water, brine), dried and concentrated. Column chromatography [silica, hexanes/EtOAc (5:1)] afforded a pale yellow liquid (1.80 g, 22%). The title compound was found to be unstable in air even as a neat liquid, but could be stored without decomposition in a degassed solution of Et$_2$O (~0.4 M) for 2 months at −20° C. Data for the title compound: $^1$H NMR δ 1.96 (s, 3H), 2.20 (s, 3H), 3.96-4.09 (m, 4H), 5.05 (s, 1H), 6.29-6.30 (m, 1H); $^{13}$C NMR δ 21.6, 28.5, 65.8, 102.7, 118.8, 161.2, 194.5; ESI-MS obsd 179.0678, calcd 179.0679 [(M+Na)$^+$, M=C$_8$H$_{12}$O$_3$]; IR (neat) 3445, 2894, 1697, 1619, 1445, 1381, 1100, 1033; IR (neat) 3525, 2978, 2893, 1697, 1618, 1445, 1380, 1236, 1162, 1101, 1033, 841 cm$^{-1}$.

1-Methoxy-4-methyl-3-penten-2-one (1e)

According to a reported procedure[41] with some modifications, a solution of α-methoxyacetic acid (6e, 1.17 g, 13.0 mmol) in anhydrous CH$_2$Cl$_2$ (20 mL) was treated portionwise with 1,1'-carbonyldiimidazole (2.54 g, 15.7 mmol) at 0° C. under argon. The ice bath was removed, and the reaction mixture was stirred for 30 min at room temperature. The reaction mixture was treated with triethylamine (2.18 mL, 15.7 mmol) and N,O-dimethylhydroxylamine hydrochloride (1.53 g, 15.6 mmol) at 0° C. The reaction mixture was stirred overnight at room temperature under argon. Saturated aqueous NH$_4$Cl was added. The organic phase was washed with water, dried (Na$_2$SO$_4$) and concentrated to a transparent oil. A solution of the crude amide was treated dropwise with 2-methyl-1-propenylmagnesium bromide (28.7 mL, 14.4 mmol, 0.5 M in THF) at −20° C. under argon. The reaction mixture was stirred for 2 h under argon at 0° C. upon which a white precipitate was formed. The mixture was diluted with Et$_2$O and treated with saturated aqueous NH$_4$Cl. The aqueous phase was extracted with ether (3×50 mL). The combined organic extract was washed (water, brine), dried (Na$_2$SO$_4$), concentrated and chromatographed [silica, hexanes/EtOAc (3:1)] to afford an orange liquid (360 mg, 22%): $^1$H NMR δ 1.93 (s, 3H), 2.20 (s, 3H), 3.43 (s, 3H), 4.01 (s, 2H), 6.19-6.20 (m, 1H); $^{13}$C NMR δ 21.4, 28.2, 59.4, 78.5, 119.6, 158.3, 197.9; ESI-MS obsd 151.0731, calcd 151.073 [(M+Na)$^+$, M=C$_7$H$_{12}$O$_2$]; IR (neat) 3451, 2979, 2935, 2825, 1699, 1618, 1447, 1379, 1227, 1200, 1109, 1038, 986, 934, 815 cm$^{-1}$.

4-Methyl-1-phenoxy-3-penten-2-one (1f)

A solution of amide 7f (508 mg, 2.60 mmol) in THF (5.1 mL) was treated dropwise with 2-methyl-1-propenylmagnesium bromide (5.70 mL, 2.85 mmol, 0.5 M in THF) at −20° C. under argon. The reaction mixture was stirred for 2 h under argon at 0° C. upon which a white precipitate formed. The mixture was diluted with Et$_2$O and treated with saturated aqueous NH$_4$Cl. The aqueous phase was extracted with ether (3×20 mL). The combined organic extract was washed (water, brine), dried (Na$_2$SO$_4$), and concentrated to a slightly yellow oil (480 mg, quantitative) of sufficient purity to not require further purification: $^1$H NMR δ 1.95 (s, 3H), 2.23 (s, 3H), 4.56 (s, 2H), 6.35-6.37 (m, 1H), 6.88 (m, 2H), 6.91-7.00 (m, 1H), 7.27-7.32 (m, 2H); $^{13}$C NMR δ 21.6, 28.4, 73.4, 114.8, 119.4, 121.7, 129.8, 159.9, 196.4; ESI-MS obsd 213.0886, calcd 213.0892 [(M+Na)$^+$, M=C$_{12}$H$_{14}$O$_2$]; IR (neat) 3520, 3041, 2911, 1702, 1686, 1600, 1495, 1436, 1379, 1211, 1152, 1121, 1031, 844, 754 cm$^{-1}$.

1-Methoxy-4-methyl-1-phenyl-3-penten-2-one (1g)

A solution of 7g (585 mg, 2.80 mmol) in THF (5.6 mL) was treated dropwise with 2-methyl-1-propenylmagnesium bromide (6.16 mL, 3.08 mmol, 0.5 M in THF) at −20° C. under argon. The reaction mixture was stirred for 2 h under argon at 0° C. The reaction mixture was diluted with Et$_2$O and treated with saturated aqueous NH$_4$Cl. The aqueous phase was extracted with ether (3×20 mL). The combined organic extract was washed (water, brine), dried (Na$_2$SO$_4$) and concentrated to a pale yellow oil. The oil, although of sufficient purity for use in subsequent reactions, was chromatographed [silica, hexanes/EtOAc (5:1)] to afford the title compound (495 mg, 87%): NMR δ 1.87 (s, 3H), 2.14 (s, 3H), 3.39 (s, 3H), 4.64 (s, 1H), 6.27-6.28 (m, 1H), 7.32-7.38 (m, 5H); $^{13}$C NMR δ 21.4, 28.3, 57.4, 89.7, 119.3, 127.1, 128.4, 128.8, 136.8, 159.4, 197.8; ESI-MS obsd 227.1041, calcd 227.1043 [(M+Na)$^+$, M=C$_{13}$H$_{16}$O$_2$]; IR (neat) 2933, 2826, 1686, 1618, 1445, 1379, 1199, 1099, 989 cm$^{-1}$.

1-(1,3-Dithiolan-2-yl)-3-methyl-2-buten-1-one (1h)

A solution of 9 (250 mg, 1.30 mmol) in THF (2.6 mL) was treated dropwise with 2-methyl-1-propenylmagnesium bromide (2.84 mL, 1.42 mmol, 0.5 M in THF) at −20° C. under argon. The reaction mixture was stirred for 2 h under argon at 0° C. upon which a light yellow precipitate formed. The mixture was diluted with Et$_2$O and treated with saturated aqueous NH$_4$Cl. The aqueous phase was extracted with ether (3×50 mL). The combined organic extract was washed (water, brine), dried (Na$_2$SO$_4$), concentrated and chromatographed [silica, hexanes/EtOAc (3:1)] to afford a yellow oil (189 mg, 77%): $^1$H NMR δ 1.95 (s, 3H), 2.19 (s, 3H), 3.31-3.35 (m, 4H), 4.87 (s, 1H), 6.23-6.24 (m, 1H); $^{13}$C NMR δ 21.4, 28.4, 39.2, 58.5, 120.3, 159.8, 193.3; ESI-MS obsd 211.0227, calcd 211.0222 [(M+Na)$^+$, M=C$_8$H$_{12}$OS$_2$]; IR (neat) 3434, 2928, 1674, 1619, 1441, 1379, 1237, 1121, 1039 cm$^{-1}$.

1-(1,3-Dioxan-2-yl)-3,3-dimethyl-4-nitro-5-(3-p-tolylpyrrol-2-yl)-1-pentanone (2c)

Following a literature procedure,[28] a mixture of 1c (268 mg, 1.58 mmol) and 10 (302 mg, 1.31 mmol) was treated overnight with DBU (0.765 mL, 3.93 mmol) at room temperature. The reaction mixture was diluted with EtOAc, and water was added; The aqueous phase was extracted with EtOAc (3×50 mL). The combined organic extract was washed (brine), dried (Na$_2$SO$_4$) and concentrated to a brown oil. Column chromatography [silica, CH$_2$Cl$_2$/EtOAc (9:1)] afforded a brown solid (186 mg, 35%): mp 145° C. (dec); $^1$H NMR δ 1.11 (s, 3H), 1.19 (s, 3H), 1.40-1.44 (m, 1H), 2.07-2.21 (m, 1H), 2.37 (s, 3H), 2.60, 2.75 (AB, J=18.8 Hz, 2H), 3.20 (ABX, J=2.5 Hz, J=15.7 Hz, 1H), 3.39 (ABX, J=11.7 Hz, J=15.4 Hz, 1H), 179-3.88 (m, 2H), 4.17-4.23 (m, 2H), 4.68 (s, 1H), 5.16 (ABX, J=2.5 Hz, J=11.7 Hz, 1H), 6.22-6.24 (m, 1H), 6.67-6.68 (m, 1H), 7.17-7.24 (m, 4H), 8.05-8.10 (br, 1H); $^{13}$C NMR δ 21.4, 24.2, 24.3, 25.4, 25.8, 36.8, 45.1, 67.3, 95.1, 100.7, 109.6, 117.7, 122.1, 123.7, 128.4, 129.5, 133.6, 135.6, 201.0; ESI-MS obsd 423.1890, calcd 423.1890 [(M+Na)$^+$, M=C$_{22}$H$_{28}$N$_2$O$_5$].

1-(1,3-Dioxolan-2-yl)-3,3-dimethyl-4-nitro-5-(3-p-tolylpyrrol-2-yl)-1-pentanone (2d)

Following a literature procedure,[28] a mixture of 1d (1.56 g, 9.99 mmol) and 10 (950 mg, 4.13 mmol) was treated with DBU (2.54 mL, 13.1 mmol) at room temperature. After 3 h, when no starting material was observed by TLC analysis, the reaction mixture was diluted with EtOAc, and water was added. The aqueous phase was extracted with EtOAc (2×50 mL). The combined organic extract was washed (brine), dried (Na$_2$SO$_4$) and concentrated to a brown oil. Column chromatography [silica, hexanes/EtOAc (3:1)] afforded a brown oil (861 mg, 54%): $^1$H NMR δ 1.11 (s, 3H), 1.20 (s, 3H), 2.37 (s, 3H), 2.50, 2.71 (AB, J=18.4 Hz, 2H), 3.19 (ABX, J=2.6 Hz, J=15.5 Hz, 1H), 3.40 (ABX, J=11.4 Hz, J=15.5 Hz, 1H), 3.98-4.03 (m, 4H), 4.93 (s, 1H), 5.13 (ABX, J=2.6 Hz, J=11.4 Hz, 1H), 6.23-6.24 (m, 1H), 6.67-6.69 (m, 1H), 7.18 (d, J=8.8 Hz, 2H), 7.26 (d, J=8.8 Hz, 2H), 8.07 (br, 1H); $^{13}$C NMR δ 21.2, 23.9, 24.1, 25.3, 36.7, 44.4, 65.7, 94.9, 102.0, 109.4, 117.7, 121.8, 123.4, 128.2, 129.3, 133.5, 135.5, 204.1; ESI-MS obsd 387.1906, calcd 387.1914 [(M+H)$^+$, M=C$_{21}$H$_{26}$N$_2$O$_5$].

1-Methoxy-4,4-dimethyl-5-nitro-6-[3-p-tolylpyrrol-2-yl]-2-hexanone (2e)

Following a literature procedure,[28] a mixture of 1e (187 mg, 1.46 mmol) and 10 (250 mg, 1.09 mmol) was treated with DBU (0.636 mL, 3.27 mmol) at room temperature. After 8 h, when no starting material was observed by TLC analysis, the reaction mixture was diluted with EtOAc, and water was added. The aqueous phase was extracted with EtOAc (4×50 mL). The combined organic extract was washed (brine), dried ($Na_2SO_4$) and concentrated to a brown oil. Column chromatography [silica, hexanes/EtOAc (3:1)] afforded a brown oil which solidified upon storage at 1° C. (274 mg, 70%): mp 103-104° C. (dec); $^1H$ NMR δ 1.09 (s, 3H), 1.20 (s, 3H), 2.37 (s, 3H), 2.36, 2.56 (AB, J=17.6 Hz, 2H), 3.22 (ABX, J=1.8 Hz, J=15.8 Hz, 1H), 3.40 (s, 3H), 3.38 (ABX, J=9.9 Hz, J=15.8 Hz, 1H), 3.90 (s, 2H), 5.14 (ABX, J=1.8 Hz, J=9.9 Hz, 1H), 6.22-6.24 (m, 1H), 6.67-6.68 (m, 1H), 7.19 (d, J=8.2 Hz, 2H), 7.23 (d, J=8.2 Hz, 2H), 8.19 (br, 1H); $^{13}C$ NMR δ 21.3, 24.2, 24.5, 25.3, 37.0, 46.5, 59.5, 78.4, 95.0, 109.5, 117.7, 122.0, 123.7, 128.4, 129.4, 133.6, 135.7, 206.8; ESI-MS obsd 381.1782, calcd 381.1785 [(M+Na)$^+$, M=$C_{20}H_{26}N_2O_4$]; Anal. Calcd for $C_{20}H_{26}N_2O_4$: C, 67.02; H, 7.31; N, 7.82. Found: C, 67.04; H, 7.25; N, 7.62.

4,4-Dimethyl-5-nitro-1-phenoxy-6-(3-p-tolylpyrrol-2-yl)-2-hexanone (2f)

Following a literature procedure,[28] a mixture of 1f (256 mg, 1.35 mmol) and 10 (250 mg, 1.09 mmol) was treated overnight with DBU (0.635 mL, 3.26 mmol) at room temperature. The reaction mixture was diluted with EtOAc, and water was added. The aqueous phase was extracted with EtOAc (4×50 mL). The combined organic extract was washed (brine), dried ($Na_2SO_4$) and concentrated to a brown oil. Column chromatography (silica, $CH_2Cl_2$) afforded a brown oil (274 mg, 60%): $^1H$ NMR δ 1.10 (s, 3H), 1.21 (s, 3H), 2.34 (s, 3H), 2.50, 2.72 (AB, J=18.2 Hz, 2H), 3.23 (ABX, J=2.7 Hz, J=15.6 Hz, 1H), 3.40 (ABX, J=11.4 Hz, J=15.6 Hz, 1H), 4.43 (d, J=3.6 Hz, 2H), 5.20 (ABX, J=2.7 Hz, J=11.4 Hz, 1H), 6.23-6.24 (m, 1H), 6.69-6.67 (m, 1H), 6.86 (d, J=8.8 Hz, 2H), 6.99-7.03 (m, 1H), 7.18-7.33 (m, 6H), 8.08 (br, 1H); $^{13}C$ NMR δ 21.3, 24.2, 24.5, 25.3, 37.0, 46.7, 73.3, 94.8, 109.5, 114.6, 117.7, 121.9, 122.1, 123.7, 128.4, 129.4, 129.9, 133.5, 135.7, 157.7, 205.6; ESI-MS obsd 443.1940, calcd 443.1941 [(M+Na)$^+$, M=$C_{25}H_{28}N_2O_4$].

1-Methoxy-4,4-dimethyl-5-nitro-6-[3-p-tolylpyrrol-2-yl]-1-phenyl-2-hexanone (2g)

Following a literature procedure,[28] a mixture of 2g (250 mg, 1.23 mmol) and 10 (235 mg, 1.02 mmol) was treated overnight with DBU (600 μL, 3.06 mmol) at room temperature. The reaction mixture was diluted with EtOAc, and water was added. The aqueous phase was extracted with EtOAc (3×50 mL). The combined organic extract was washed (brine), dried ($Na_2SO_4$) and concentrated to a brown oil. Column chromatography [silica, hexanes/EtOAc (5:1)] afforded a brown oil (280 mg, 63%, a mixture of diastereomers): $^1H$ NMR δ 0.96 (s, 3H), 0.97 (s, 3H), 1.04 (s, 3H), 1.09 (s, 3H), 2.36 (s, 3H), 2.37 (s, 3H), 2.40 (m, 2H), 2.56-2.62 (m, 1H), 2.69-2.75 (m, 1H), 3.09-3.12 (m 1H), 3.14-3.18 (m, 1H), 3.29-3.33 (m, 2H), 3.35 (s, 3H), 3.36 (s, 3H), 4.57 (s, 1H), 4.58 (s, 1H), 5.14-5.15 (m, 1H), 5.17-5.19 (m, 1H) 6.21-6.22 (m, 2H), 6.64-6.67 (m, 2H), 7.14-7.25 (m, 8H), 7.31-7.40 (m, 10H), 8.03 (br, 1H), 8.07 (br, 1H); $^{13}C$ NMR δ 21.23, 21.25, 23.95, 23.99, 24.04, 24.2, 25.3, 25.4, 36.8, 36.9, 45.1, 45.5, 57.35, 57.42, 89.7, 89.8, 95.0, 95.1, 109.4, 109.5, 117.65, 117.66, 122.96, 122.0, 123.5, 123.6, 127.2, 127.4, 128.25, 128.33, 128.89, 128.98, 129.01, 129.1, 129.3, 133.59, 133.61, 135.5, 135.6, 206.4, 206.7; ESI-MS obsd 435.2275, calcd 435.2278 [(M)$^+$, M=$C_{26}H_{30}N_2O$].

1-(1,3-Dithiolan-2-yl)-3,3-dimethyl-4-nitro-5-(3-p-tolylpyrrol-2-yl)-1-pentanone (2h)

Following a literature procedure,[28] a mixture of 1h (180 mg, 0.958 mmol) and 10 (200 mg, 0.869 mmol) was treated with DBU (0.508 mL, 2.61 mmol) at room temperature. After 3.5 h, when no starting material was observed by TLC analysis, the reaction mixture was diluted with EtOAc, and water (50 mL) and aqueous saturated solution of $NH_4Cl$ (50 mL) were added. The aqueous phase was extracted with EtOAc (3×70 mL). The combined organic extract was washed (brine), dried ($Na_2SO_4$) and concentrated to a brown oil. Column chromatography [silica, hexanes/EtOAc (3:1)] afforded a brown oil (129 mg, 36%): $^1H$ NMR (400 MHz) δ 1.12 (s, 3H), 1.16 (s, 3H), 2.37 (s, 3H), 2.63, 2.76 (AB, J=18.0 Hz, 2H), 3.23 (ABX, J=2.8 Hz, J=15.6 Hz, 1H), 3.25-3.32 (m, 4H), 3.38 (ABX, J=11.4 Hz, J=15.4 Hz, 1H), 4.74 (s, 1H), 5.14 (ABX, J=2.8 Hz, J=11.4 Hz, 1H), 6.22-6.23 (m, 1H), 6.66-6.68 (m, 1H), 7.18 (d, J=8.4 Hz, 2H), 7.23 (d, J=8.4 Hz, 2H), 8.12 (br, 1H); $^{13}C$ NMR δ 21.6, 24.4, 24.5, 25.7, 37.6, 39.4, 46.4, 58.6, 95.6, 109.9, 118.1, 122.3, 123.9, 128.6, 129.7, 133.9, 136.0, 202.1; ESI-MS obsd 419.1458, calcd 419.1453 [(M+H)$^+$, M=$C_{21}H_{26}N_2O_3$].

1-(1,3-Dioxan-2-yl)-2,3-dihydro-3,3-dimethyl-7-p-tolyldipyrrin (3c)

Following a reported procedure,[28] in a first flask a solution of 2c (255 mg, 0.422 mmol) in THF/MeOH (2 mL, 5:1) was treated with NaOMe (114 mg, 2.11 mmol) with bubbling with argon at 0° C. The mixture was stirred for 30 min at 0° C. with bubbling with argon. In a second flask, $TiCl_3$ (20 wt % $TiCl_3$ in 3 wt % HCl, 1.60 mL, 2.54 mmol) in THF (5 mL) was treated with a solution of $NH_4Cl$ (1.30 g, 16.9 mmol) in $H_2O$ (2.5 mL) that had been bubbled with argon for 1 h. The solution from the first flask was transferred to the buffered $TiCl_3$ mixture in the second flask. The resulting reaction mixture was stirred overnight under argon at room temperature. Ethyl acetate and water were added. The organic extract was washed (brine), dried ($Na_2SO_4$), concentrated and chromatographed [silica, hexanes/EtOAc (2:1)] to afford a light yellow solid (27 mg, 18%): mp 45° C.; $^1H$ NMR (400 MHz) δ 1.18 (s, 6H), 1.44-1.47 (m, 1H), 2.17-2.23 (m, 1H), 2.38 (s, 3H), 2.67 (s, 2H), 3.92-3.98 (m, 2H), 4.21-4.24 (m, 2H), 5.39 (s, 1H), 6.10 (s, 1H), 6.26-6.28 (m, 1H), 6.85-6.87 (m, 1H), 7.21 (d, J=8.3 Hz, 2H), 7.34 (d, J=8.3 Hz, 2H), 10.92 (br, 1H); $^{13}C$ NMR δ 21.4, 26.0, 29.3, 40.4, 48.0, 67.3, 99.9, 106.6, 109.1, 119.3, 124.6, 126.9, 128.7, 129.4, 134.3, 135.3, 160.2, 173.4; ESI-MS obsd 351.2064, calcd 351.2067 [(M+H)$^+$, M=$C_{22}H_{26}N_2O_2$].

1-(1,3-Dioxolane-2-yl)-2,3-dihydro-3,3-dimethyl-7-p-tolyldipyrrin (3d)

Following a reported procedure,[28] in a first flask a solution of 2d (940 mg, 2.43 mmol) in THF/MeOH (11.4 mL, 5:1) was treated with NaOMe (395 mg, 7.32 mmol) at 0° C. under argon. The mixture was stirred for 40 min at 0° C. under argon. In a second flask, $TiCl_3$ (20 wt % $TiCl_3$ in 3 wt % HCl, 9.30 mL, 14.7 mmol) in THF (9.5 mL) was treated with a solution of $NH_4Cl$ (7.52 g, 97.7 mmol) in $H_2O$ (6.0 mL) that had been bubbled with argon for 1 h. The solution from the first flask was transferred to the buffered $TiCl_3$ mixture in the second flask while bubbling with argon. The resulting reaction mixture was stirred overnight under argon at room temperature. Ethyl acetate and water were added. The organic extract was washed (brine), dried ($Na_2SO_4$), and chromatographed [alumina, hexanes/EtOAc (3:1)] to afford a yellow solid (255 mg, 31%): mp 185° C. (dec); $^1$H NMR (400 MHz) δ 1.20 (s, 6H), 2.39 (s, 3H), 2.61 (s, 2H), 4.01-4.12 (m, 4H), 5.64 (s, 1H), 6.10 (s, 1H), 6.26-6.29 (m, 1H), 6.85-6.87 (m, 1H), 7.21 (d, J=8.1 Hz, 2H), 7.36 (d, J=8.1 Hz, 2H), 10.82 (br, 1H); $^{13}$C NMR δ 21.3, 29.2, 40.7, 47.1, 66.0, 101.4, 106.6, 109.2, 119.4, 124.8, 126.8, 128.7, 129.4, 134.2, 135.4, 160.0, 173.4; ESI-MS obsd 337.1911, calcd 337.1911 [(M+H)$^+$, M=$C_{21}H_{24}N_2O_2$].

2,3-Dihydro-1-(methoxymethyl)-3,3-dimethyl-7-p-tolyldipyrrin (3e)

Following a reported procedure,[28] in a first flask a solution of 2e (150 mg, 0.419 mmol) in THF/MeOH (1.95 mL, 5:1) was treated with NaOMe (68 mg, 1.3 mmol) and bubbled with argon at 0° C. The mixture was stirred for 30 min at 0° C. and bubbled with argon. In a second flask, TiCl$_3$ (20 wt % TiCl$_3$ in 3 wt % HCl, 1.59 mL, 2.52 mmol) in THF (5.0 mL) was treated with a solution of NH$_4$Cl (1.29 g, 16.8 mmol) in H$_2$O (2 mL) that had been bubbled with argon for 1 h. The solution from the first flask was transferred to the buffered TiCl$_3$ mixture in the second flask. The resulting reaction mixture was stirred overnight (15 h) under argon at room temperature. Ethyl acetate and water were added. The organic extract was washed (brine), dried (K$_2$CO$_3$), concentrated and chromatographed [alumina, hexanes/EtOAc (5:1)] to afford a brown solid (28 mg, 22%). Note that the title compound decomposed upon attempted column chromatography on silica gel. Data for the title compound: mp 93-95° C.; $^1$H NMR δ 1.20 (s, 6H), 2.39 (s, 3H), 2.61 (s, 2H), 3.44 (s, 3H), 4.33 (s, 2H), 6.06 (s, 1H), 6.27-6.30 (m, 1H), 6.85-6.87 (m, 1H), 7.21 (d, J=7.8 Hz, 2H), 7.35 (d, J=7.8 Hz, 2H), 10.90 (br, 1H); $^{13}$C NMR δ 21.7, 29.7, 41.0, 50.6, 59.6, 73.3, 105.3, 109.5, 119.2, 124.5, 127.4, 129.0, 129.7, 134.7, 135.6, 160.8, 176.8; ESI-MS obsd 309.1971, calcd 309.1961 [(M+H)$^+$, M=$C_{20}H_{24}N_2O$].

2,3-Dihydro-3,3-dimethyl-1-(phenoxymethyl)-7-p-tolyldipyrrin (3l)

Following a reported procedure,[28] in a first flask a solution of 2f (270 mg, 0.642 mmol) in THF/MeOH (3.5 mL, 5:1) was treated with NaOMe (174 mg, 3.22 mmol) and bubbled with argon at 0° C. The mixture was stirred for 30 min at 0° C. and bubbled with argon. In a second flask, TiCl$_3$ (20 wt % TiCl$_3$ in 3 wt % HCl, 2.4 mL, 3.80 mmol) in THF (7.7 mL) was treated with a solution of NH$_4$Cl (1.98 g, 25.7 mmol) in H$_2$O (5 mL) that had been bubbled with argon for 1 h. The solution from the first flask was transferred to the buffered TiCl$_3$ mixture in the second flask. The resulting reaction mixture was stirred overnight under argon at room temperature. Ethyl acetate and water were added. The organic extract was washed (brine), dried (Na$_2$SO$_4$), concentrated and chromatographed [silica, CH$_2$Cl$_2$/hexanes (1:1)] to afford a light brown oil which quickly turned dark brown (87.5 mg, 37%): $^1$H NMR δ 1.18 (s, 6H), 2.39 (s, 3H), 2.66 (s, 2H), 4.97 (s, 2H), 6.07 (s, 1H), 6.28-6.30 (m, 1H), 6.82-6.84 (m, 1H), 6.94-6.98 (m, 3H), 7.20-7.23 (d, J=7.7 Hz, 2H), 7.29-7.37 (m, 4H), 10.78 (br, 1H); $^{13}$C NMR δ 21.4, 29.3, 40.8, 50.3, 68.3, 105.3, 109.3, 114.8, 119.1, 121.7, 122.7, 124.4, 128.7, 129.4, 129.9, 134.3, 135.4, 160.3, 175.4; ESI-MS obsd 371.2105, calcd 371.2118 [(M+H)$^+$, M=$C_{25}H_{27}N_2O$].

Dimethoxyacetonitrile (5)

According to a general procedure for the title compound (but without characterization data)[38] carried out at 8-fold larger scale, trimethyl orthoformate (27.6 mL, 252 mmol) and trimethylsilyl cyanide (34.0 mL, 255 mmol) were placed in a two-neck round-bottom flask equipped with a stirring bar and a water condenser (all oven-dried) under argon. The contents of the flask were treated dropwise with BF$_3$.OEt$_2$ (3.1 mL, 25 mmol) under argon at room temperature. An exotherm ensued accompanied by ether reflux. The reaction mixture was stirred for 3 h at room temperature whereupon saturated aqueous NaHCO$_3$ (200 mL) was added. The aqueous phase was extracted with ether (3×75 mL). The combined organic extract was dried (Na$_2$SO$_4$) and filtered. The filtrate was concentrated and distilled (oil bath 150° C.) to afford a transparent liquid (22.9 g, 90%): ESI-MS obsd 102.0552, calcd 102.0550 [(M+H)$^+$, M=$C_4H_7NO_2$]. The characterization values ($^1$H NMR) were consistent with those in the literature.[39]

N-Methoxy-N-methyl-2-phenoxyacetamide (7f)

According to a reported procedure[41] with some modifications, a solution of phenoxyacetic acid (6f, 1.00 g, 6.57 mmol) in anhydrous CH$_2$Cl$_2$ (10 mL) was treated portionwise with 1,1'-carbonyldiimidazole (1.39 g, 8.57 mmol) at 0° C. under argon. The ice bath was removed, and the reaction mixture was stirred for 30 min at room temperature. The reaction mixture was treated with triethylamine (1.3 mL, 9.3 mmol) and N,O-dimethylhydroxylamine hydrochloride (0.90 g, 9.2 mmol) at 0° C. The reaction mixture was stirred overnight at room temperature under argon. 1 M HCl (10 mL) was added. The organic phase was washed (water), dried (Na$_2$SO$_4$) and concentrated to a transparent oil. Column chromatography [silica, hexanes/EtOAc (1:1)] afforded a transparent oil (1.18 g, 91%). The characterization values ($^1$H NMR) were consistent with those in the literature.[41]

N-Methoxy-N-methyl-2-methoxy-2-phenylacetamide (7g)

According to a reported procedure with some modifications,[41] a solution of α-methoxyphenylacetic acid (6g, 1.00 g, 6.02 mmol) in anhydrous CH$_2$Cl$_2$ (9.0 mL) was treated portionwise with 1,1'-carbonyldiimidazole (1.27 g, 7.83 mmol) at 0° C. under argon. The ice bath was removed, and the reaction mixture was stirred for 40 min at room temperature. The reaction mixture was treated with triethylamine (1.2 mL, 8.6 mmol) and N,O-dimethylhydroxylamine hydrochloride (826 mg, 8.43 mmol) at 0° C. The reaction mixture was stirred overnight at room temperature under argon. A sample of 1 M HCl (10 mL) was added. The organic extract was washed with water, dried (Na$_2$SO$_4$) and concentrated to give a transparent oil. Column chromatography [silica, hexanes/EtOAc (1:1)] afforded a transparent oil (735 mg, 58%): $^1$H NMR δ 3.17 (s, 3H), 3.39 (s, 3H), 3.42 (br, 3H), 5.12 (s, 1H), 7.32-7.39 (m, 3H), 7.44-7.46 (m, 2H); $^{13}$C NMR δ 32.6, 57.4, 61.2, 81.0, 127.5, 128.4, 128.9, 136.7, 172.0; IR (Et$_2$O) 3504, 2938, 2823, 1675, 1455, 1385, 1197, 1176, 1111 cm$^{-1}$; ESI-MS obsd 232.0952, calcd 232.0944 [(M+Na)$^+$, M=$C_{11}H_{15}O_3$]; IR (neat) 3504, 2938, 2823, 1675, 1455, 1385, 1197, 1176, 1111 cm$^{-1}$.

N-Methoxy-N-methyl-1,3-dithiolane-2-carboxamide (9)

A vigorously stirred slurry of ethyl 1,3-dithiolane-2-carboxylate (8, 1.50 mL, 10.5 mmol) and N,O-dimethylhydroxylamine hydrochloride (2.57 g, 26.2 mmol) in THF (21 mL) was treated dropwise with isopropylmagnesium bromide (52.5 mmol, 26.3 mL, 2 M in THF) over 40 min at −78°

C. under argon. The reaction mixture was stirred for 1 h at −78° C. under argon. The reaction mixture was quenched with saturated aqueous NH$_4$Cl/H$_2$O (1:1). The aqueous phase was extracted with ether (3×100 mL). The combined organic extract was washed (water, brine), dried (Na$_2$SO$_4$), concentrated and chromatographed [silica, EtOAc/hexanes (2:1)] to afford a yellow oil that solidified upon storage at 1° C. (985 mg, 49%). The characterization values ($^1$H NMR, $^{13}$C NMR, ESI-MS) were consistent with those for the title compound prepared via a different synthetic route.[43]

Self-Condensation Study.

Following a general procedure,[46] a solution of a hydrodipyrrin (0.014-0.047 mmol, 18 mM) and 2,6-DTBP (8 mol equiv) in anhydrous CH$_2$Cl$_2$ was treated with TMSOTf (4 molar equiv) at room temperature. The reaction mixture was stirred overnight. The reaction mixture was diluted with CH$_2$Cl$_2$ and quenched with saturated aqueous NaHCO$_3$. After extraction, the organic phase was washed (water, brine), dried (Na$_2$SO$_4$) and concentrated. The crude sample was analyzed for the presence of bacteriochlorin macrocycles by TLC, LD-MS and UV-Vis spectroscopy. The data are shown in Table 2.

8,8,18,18-Tetramethyl-2,12-di-p-tolyl-5-[2-(trimethylsilyloxy)ethoxy]bacteriochlorin (BC-3)

Following a general procedure,[46] a solution of 3d (255 mg, 0.758 mmol) and 2,6-DTBP (1.36 mL, 6.06 mmol) in CH$_2$Cl$_2$ (42 mL) was treated with TMSOTf (0.55 mL, 3.04 mmol) at room temperature. The reaction mixture was stirred for 22 h at room temperature. The reaction mixture was diluted with CH$_2$Cl$_2$ and quenched with saturated aqueous NaHCO$_3$. After extraction, the organic phase was washed (water, brine), dried (Na$_2$SO$_4$) and concentrated. Column chromatography [silica, CH$_2$Cl$_2$/hexanes (1:1)] afforded a green solid (77 mg, 30%); $^1$H NMR δ −1.92 (br, 1H), −1.80 (br, 1H), 0.34 (s, 9H), 1.89 (s, 6H), 1.91 (s, 6H), 2.61 (s, 6H), 4.31-4.34 (m, 2H), 4.38 (s, 2H), 4.43 (s, 2H), 4.65-4.68 (m, 2H), 7.56-7.58 (m, 4H), 8.08-8.15 (m, 4H), 8.68 (s, 2H), 8.78 (s, 1H), 8.81 (s, 1H), 9.07-9.08 (m, 1H); $^{13}$C NMR δ 0.22, 21.6, 31.10, 31.16, 45.94, 46.18, 47.9, 51.9, 62.6, 76.8, 79.3, 95.7, 95.8, 97.8, 116.8, 121.0, 129.9, 130.0, 130.3, 131.1, 131.3, 133.2, 133.8, 134.1, 134.2, 134.4, 134.8, 135.6, 137.0, 137.2, 137.5, 153.4, 159.6, 169.6, 170.0; LD-MS obsd 681.8; ESI-MS obsd 683.3762, calcd 683.3776 [(M+H)$^+$, M=C$_{43}$H$_{50}$N$_4$O$_2$Si]; λ$_{abs}$ 355, 374, 512, 732 nm.

5-(2-Hydroxyethoxy)-8,8,18,18-tetramethyl-2,12-di-p-tolylbacteriochlorin (BC-4)

A solution of BC-3 (20 mg, 0.029 mmol) in THF (3.0 mL) was treated with TBAF (44 μL, 0.044 mmol, 1 M in THF) under argon at room temperature. The reaction mixture was stirred at room temperature under argon. After 45 min, no starting material was observed by TLC analysis. Water and CH$_2$Cl$_2$ were added. The organic extract was washed (brine), dried (Na$_2$SO$_4$), concentrated and chromatographed (silica, CH$_2$Cl$_2$) to afford a green solid (15 mg, 83%); $^1$H NMR δ −1.85 (br, 1H), −1.75 (br, 1H), 1.90 (s, 6H), 1.91 (s, 6H), 2.60 (s, 3H), 2.61 (s, 3H), 2.62-2.68 (m, 1H), 4.31-4.37 (m, 2H), 4.40 (s, 4H), 4.69-4.71 (m, 2H), 7.55-7.59 (m, 4H), 8.08-8.12 (m, 4H), 8.67 (s, 2H), 8.77 (s, 1H), 8.80 (s, 1H), 8.94 (s, 1H); 21.61, 21.64, 31.05, 31.20, 46.0, 46.3, 47.8, 52.1, 63.1, 78.9, 95.8, 96.0, 98.0, 116.0, 121.4, 129.8, 129.97, 130.03, 131.1, 131.3, 133.0, 133.6, 133.7, 134.2, 134.3, 135.3, 136.0, 137.1, 137.6, 137.7, 152.6, 160.1, 169.6, 170.3; LD-MS 610.0; ESI-MS obsd 611.3365, calcd 611.3381 [(M+H)$^+$, M=C$_{40}$H$_{42}$N$_4$O$_2$]; λ$_{abs}$ 355, 374, 511, 731 nm 15-Bromo-5-(2-hydroxyethoxy)-8,8,18,18-tetramethyl-2,12-di-p-tolylbacteriochlorin (BC-5)

A sample of BC-4 (14 mg, 0.023 mmol) in THF (11.5 mL) was treated with NBS (0.23 mL, 0.023 mmol, 100 mM in THF) at room temperature. After stirring for 1 h, water and CH$_2$Cl$_2$ were added. The organic extract was washed (brine), dried (Na$_2$SO$_4$) and concentrated. Column chromatography (silica, CH$_2$Cl$_2$) afforded a green solid (10 mg, 64%); NMR (400 MHz, THF-d$_8$) δ −2.01 (br, 1H), −1.82 (br, 1H), 1.90 (s, 12H), 2.47 (s, 6H), 4.17-4.22 (m, 2H), 4.47 (s, 2H), 4.47-4.50 (m, 1H), 4.51 (s, 2H), 4.67 (t, J=4.4 Hz, 2H), 7.55-7.59 (m, 4H), 8.06-8.11 (m, 4H), 8.77 (s, 1H), 8.82 (s, 1H), 8.98-8.99 (m, 1H), 9.04-9.05 (m, 1H); $^{13}$C NMR (THF-d$_8$) δ 21.6, 31.3, 31.5, 46.4, 46.9, 49.0, 55.0, 62.9, 81.3, 96.4, 98.4, 119.5, 121.6, 129.1, 129.8, 130.67, 130.70, 132.0, 132.1, 133.1, 133.9, 134.0, 134.6, 134.8, 135.4, 135.8, 137.0, 137.6, 138.1, 138.3, 158.0, 158.7, 169.1, 172.9; LD-MS, 688.4; ESI-MS obsd 711.2297, calcd 711.2305 [(M+Na)$^+$, M=C$_{40}$R$_{41}$BrN$_4$O$_2$]; λ$_{abs}$ 362, 378, 524, 734 nm.

Direct Conversion of BC-3 to BC-5.

A sample of BC-3 (73 mg, 0.11 mmol) in THF (53.5 mL) was treated with NBS (19 mg, 0.11 mmol) at room temperature. After stirring for 1 h at room temperature, the reaction mixture was quenched with water. After extraction with CH$_2$Cl$_2$, the organic phase was washed (brine), dried (Na$_2$SO$_4$) and concentrated. Column chromatography (silica, CH$_2$Cl$_2$) afforded a green solid (48 mg, 65%). The characterization values ($^1$H NMR, LD-MS) were consistent with those reported above.

Elaboration of the 2-hydroxyethoxy Group and/or 15-halo Group to Create Diverse trans-AB-bacteriochlorins The desired attributes of the bacteriochlorins for applications in the biosciences and medicine are water-solubility, bioconjugatability, and wavelength-tunability (Scheme 11, right). So far no bacteriochlorin carrying all these functions has been prepared due to limitations of synthesis, regardless of whether one employs de novo or semisynthetic methods. A new building block 5-(2-hydroxyethoxy)bacteriochlorin, however, can be endowed with all three attributes. The methodology for synthesis of the 5-(2-hydroxyethoxy)bacteriochlorin allows introduction of various substituents during different steps of the synthesis. First, one type of substituent (e.g., auxochromes) can be introduced in the dihydrodipyrrin precursor, as shown by the R group in Scheme 11 (left).

Scheme 11. Generic features of a bacteriochlorin for a biomedical application.
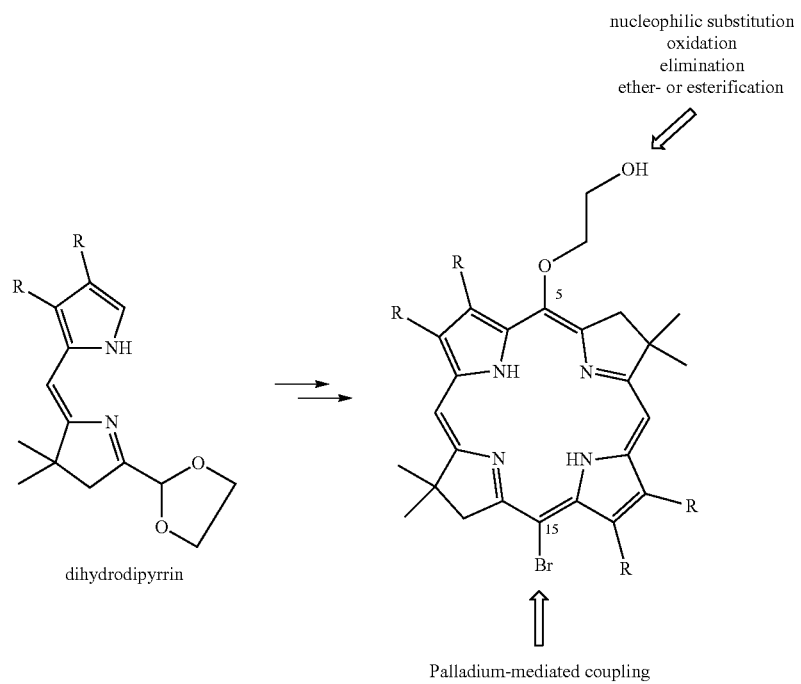
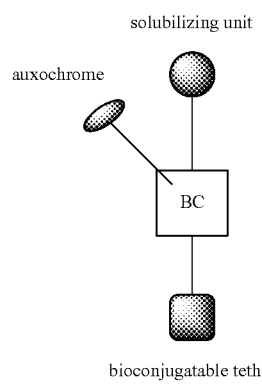

Second, the hydroxyl group of the 2-hydroxyethoxy moiety presents a versatile handle for chemical transformations: nucleophilic substitution, oxidation, elimination, esterification, etherification. Examples of the transformations of the hydroxy group include but are not limited to the following shown in Scheme 12:

Scheme 12. Examples of elaboration of the 2-hydroxyethoxy group of the bacteriochlorin.

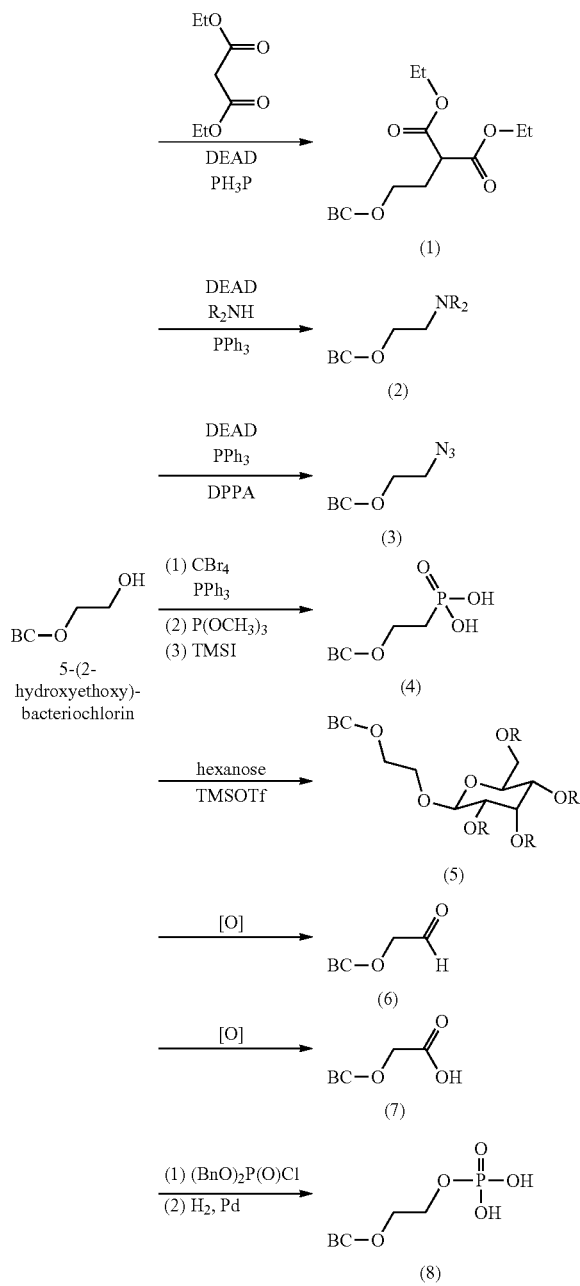

(i) nucleophilic substitution, for example, the Mitsunobu reaction with various O-, S-, N-, and C-nucleophiles to introduce malonates (entry 1, water-solubilization) or amines (entry 2, quaternization or acylation), azides (entry 3, click chemistry components), Appel reaction to afford, for example, phosphonates (entry 4, water-solubilizing group);

(ii) etherifications with oligosaccharide (entry 5, biomedically relevant group);

(iii) oxidation to afford an aldehyde (entry 6, water-solubilizing and bioconjugatable group via reductive amination) or carboxylic acid (entry 7, water-solubilizing and bioconjugatable group).

In the transformation shown, DEAD refers to diethyl azodicarboxylate; DPPA refers to diphenylphosphoryl azide; TMSI refers to trimethylsilyl iodide; TMSOTf refers to trimethylsilyl triflate; and [O] refers to a variety of oxidants. Preferred oxidants ([O]) for conversion to the aldehyde include Dess-Martin periodinane or TEMPO or $MnO_2$ or PCC or $CrO_3$/pyridine. Preferred oxidants for conversion to the carboxylic acid include Jones reagent or $KMnO_4$ or TEMPO/NaOCl or PDC/DMF.

A particularly desirable transformation entails coupling of the hydroxy moiety with 2,4,6-trichloro-1,3,5-triazine (cyanuric chloride) to form the ether followed by successive displacement of the remaining two chlorides with amines ($H_2NR$) as shown in Scheme 13. One example employs taurine (2-aminoethylsulfonic acid) as the $H_2NR$ moiety to create a water-solubilizing unit.

Scheme 13. Triazine chemistry for elaboration of the bacteriochlorin 2-hydroxyethoxy group.

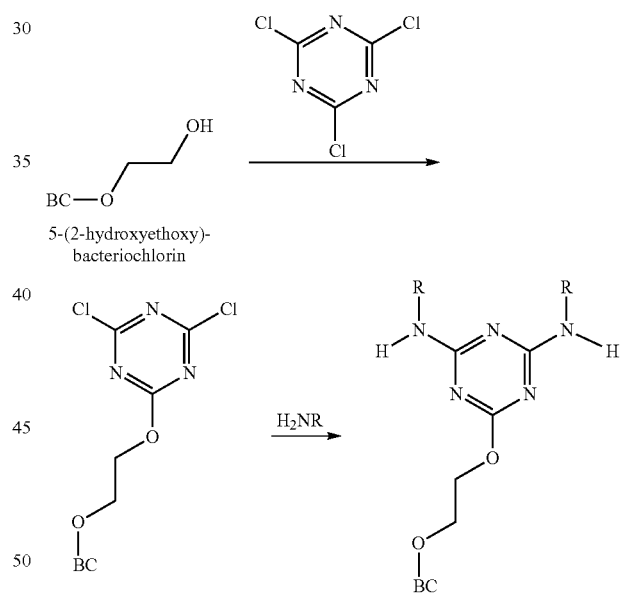

Third, the 15-halo group can be elaborated by means of palladium-mediated coupling (Stille, Sonagoshira, Hartwig-Buchwald, Suzuki) as shown in Table 3. Entry 1 affords a pyridine unit, which upon quaternization affords a polar moiety that may facilitate water solubilization. Entry 2 affords a bioconjugatable group directly. Entry 3 affords an anilino group, which can be derivatized in numerous ways. One example is acylation with succinic anhydride, thereby affording the amide with a free carboxylic acid. Entries 7 and 8 afford carbonyl units, which upon reductive amination with appropriate amines afford tethers for water solubilization or bioconjugation.

TABLE 3

Examples of elaboration of the 15-bromo group by means of palladium-coupling.

| Entry | R$^{15}$ | Palladium-mediated Reaction |
|---|---|---|
| 1 | 4-pyridyl | Suzuki Coupling |
| 2 | 4-COOH-phenyl | Suzuki Coupling |
| 3 | 3-NH$_2$-phenyl | Suzuki Coupling |
| 4 | —C≡C—TIPS | Sonagoshira Coupling |
| 5 | —C≡C-phenyl | Sonagoshira Coupling |
| 6 | 3-(PhC(O)NH)- | Hartwig-Buchwald Coupling |
| 7 | —C(O)CH$_3$ | Stille Coupling |
| 8 | —C(O)H | Palladium-mediated Carbonylation |

REFERENCES (1) Lindsey, J. S. *Acc. Chem. Res.* 2010, 43, 300-311.
(2) Senge, M. O. *Chem. Commun.* 2011, 47, 1943-1960.
(3) Ptaszek, M.; Lahaye, D.; Krayer, M.; Muthiah, C.; Lindsey, J. S. *J. Org. Chem.* 2010, 75, 1659-1673.
(4) Galezowski, M.; Gryko, D. T. *Curr. Org. Chem.* 2007, 11, 1310-1338.
(5) Taniguchi, M.; Cramer, D. L.; Bhise, A. D.; Kee, H. L.; Bocian, D. F.; Holten, D.; Lindsey, J. S. *New J. Chem.* 2008, 32, 947-958.
(6) Yang, E.; Kirmaier, C.; Krayer, M.; Taniguchi, M.; Kim, H.-J.; Diers, J. R.; Bocian, D. F.; Lindsey, J. S.; Holten, D. *J. Phys. Chem. B* 2011, 115, 10801-10816.
(7) Lindsey, J. S.; Mass, O.; Chen, C.-Y. *New J. Chem.* 2011, 35, 511-516.
(8) Wasielewski, M. R.; Svec, W. A. *J. Org. Chem.* 1980, 45, 1969-1974.
(9) Osuka, A.; Wada, Y.; Maruyama, K.; Tamiaki, H. *Heterocycles* 1997, 44, 165-168.
(10) Fukuzumi, S.; Ohkubo, K.; Chen, Y.; Pandey, R. K.; Zhan, R.; Shao, J.; Kadish, K. M. *J. Phys. Chem. A* 2002, 106, 5105-5113.
(11) Mironov, A. F.; Grin, M. A.; Tsiprovskiy, A. G.; Kachala, V. V.; Karmakova, T. A.; Plyutinskaya, A. D.; Yakubovskaya, R. I. *J. Porphyrins Phthalocyanines* 2003, 7, 725-730.
(12) Sasaki, SA; Tamiaki, H. *J. Org. Chem.* 2006, 71, 2648-2654.
(13) Grin, M. A.; Mironov, A. F.; Shtil, A. A. *Anti-Cancer Agents Med. Chem.* 2008, 8, 683-697.
(14) Tamiaki, H.; Kunieda, M. In *Handbook of Porphyrin Science*; Kadish, K. M., Smith, K. M., Guilard, R., Eds.; World Scientific Publishing Co.: Singapore, Vol. 11, 2011, pp 223-290.
(15) Dorough, G. D.; Miller, J. R. *J. Am. Chem. Soc.* 1952, 74, 6106-6108.
(16) Whitlock, H. W., Jr.; Hanauer, R.; Oester, M. Y.; Bower, B. K. *J. Am. Chem. Soc.* 1969, 91, 7485-7489.
(17) Shea, K. M.; Jaquinod, L.; Khoury, R. G.; Smith, K. M. *Tetrahedron* 2000, 56, 3139-3144.
(18) Chen, Y.; Li, G.; Pandey, R. K. *Curr. Org. Chem.* 2004, 8, 1105-1134.
(19) Pereira, N. A. M.; Serra, A. C.; Pinho e Melo, T. M. V. D. *Eur. J. Org. Chem.* 2010, 6539-6543.
(20) Samankumara, L. P.; Zeller, M.; Krause, J. A.; Brückner, C. *Org. Biomol. Chem.* 2010, 8, 1951-1965.
(21) Singh, S.; Aggarwal, A.; Thompson, S.; Tomé, J. P. C.; Zhu, X.; Samaroo, D.; Vinodu, M.; Gao, R.; Drain, C. M. *Bioconjugate Chem.* 2010, 21, 2136-2146.

(22) Pereira, N. A. M.; Fonseca, S. M.; Serra, A. C.; Pinho e Melo, T. M. V. D.; Burrows, H. D. *Eur. J. Org. Chem.* 2011, 3970-3979.
(23) Minehan, T. G.; Cook-Blumberg, L.; Kishi, Y.; Prinsep, M. R.; Moore, R. E. *Angew. Chem. Int. Ed.* 1999, 38, 926-928.
(24) Wang, W.; Kishi, Y. *Org. Lett.* 1999, 1, 1129-1132.
(25) Kim, H.-J.; Lindsey, J. S. *J. Org. Chem.* 2005, 70, 5475-5486.
(26) Ruzié, C.; Krayer, M.; Balasubramanian, T.; Lindsey, J. S. *J. Org. Chem.* 2008, 73, 5806-5820.
(27) Krayer, M.; Balasubramanian, T.; Ruzié, C.; Ptaszek, M.; Cramer, D. L.; Taniguchi, M.; Lindsey, J. S. *J. Porphyrins Phthalocyanines* 2009, 13, 1098-1110.
(28) Krayer, M.; Ptaszek, M.; Kim, H.-J.; Meneely, K. R.; Fan, D.; Secor, K.; Lindsey, J. S. *J. Org. Chem.* 2010, 75, 1016-1039.
(29) Krayer, M.; Yang, E.; Diers, J. R.; Bocian, D. F.; Holten, D.; Lindsey, J. S. *New J. Chem.* 2011, 35, 587-601.
(30) Ogikubo, J.; Brückner, C. *Org. Lett.* 2011, 13, 2380-2383.
(31) Sutton, J. M.; Clarke, O. J.; Fernandez, N.; Boyle, R. W. *Bioconjugate Chem.* 2002, 13, 249-263.
(32) Kobayashi, M.; Akiyama, M.; Kano, H.; Kise, H. In *Chlorophylls and Bacteriochlorophylls: Biochemistry, Biophysics, Functions and Applications*; Grimm, B.; Porra, R. J.; Rüdiger, W.; Scheer, H., Eds.; Springer: Dordrecht, The Netherlands, 2006, pp 79-94.
(33) Fan, D.; Taniguchi, M.; Lindsey, J. S. *J. Org. Chem.* 2007, 72, 5350-5357.
(34) Tiecco, M.; Testaferri, L.; Tingoli, M.; Bartoli, D. *J. Org. Chem.* 1990, 55, 4523-4528.
(35) Mentzel, M.; Hoffmann, H. M. R. *J. Prakt. Chem.* 1997, 339, 517-524.
(36) Williams, J. M.; Jobson, R. B.; Yasuda, N.; Marchesini, G.; Dolling, U.-H.; Grabowski, E. J. J. *Tetrahedron Lett.* 1995, 36, 5461-5464.
(37) Pereira, C. L.; Chen, Y.-H.; McDonald, F. E. *J. Am. Chem. Soc.* 2009, 131, 6066-6067.
(38) Utimoto, K.; Wakabayashi, Y.; Shishiyama, Y.; Inoue, M.; Nozaki, H. *Tetrahedron Lett.* 1981, 22, 4279-4280.
(39) Kirchmeyer, S.; Mertens, A.; Arvanaghi, M.; Olah, G. A. *Synthesis* 1983, 498-500.
(40) Suzuki, H.; Sakai, N.; Iwahara, R.; Fujiwaka, T.; Satoh, M.; Kakehi, A.; Konakahara, T. *J. Org. Chem.* 2007, 72, 5878-5881.
(41) Beutner, G. L.; Kuethe, J. T.; Kim, M. M; Yasuda, N. *J. Org. Chem.* 2009, 74, 789-794.
(42) Kawabata, T.; Yahiro, K.; Fuji, K. *J. Am. Chem. Soc.* 1991, 113, 9694-9696.
(43) Balasubramaniam, S.; Aidhen, I. S. *Synlett* 2007, 959-963.
(44) Taniguchi, M.; Ra, D.; Mo, G.; Balasubramanian, T.; Lindsey, J. S. *J. Org. Chem.* 2001, 66, 7342-7354.
(45) Kim, H.-J.; Dogutan, D. K.; Ptaszek, M.; Lindsey, J. S. *Tetrahedron* 2007, 63, 37-55.
(46) Krayer, M.; Yang, E.; Kim, H.-J.; Kee, H. L.; Deans, R. M.; Sluder, C. E.; Diers, J. R.; Kirmaier, C.; Bocian, D. F.; Holten, D.; Lindsey, J. S. *Inorg. Chem.* 2011, 50, 4607-4618.
(47) Aravindu, K.; Krayer, M.; Kim, H.-J.; Lindsey, J. S. *New J. Chem.* 2011, 35, 1376-1384.

The foregoing is illustrative of the present invention, and is not to be construed as limiting thereof. The invention is defined by the following claims, with equivalents of the claims to be included therein.

That which is claimed is:

1. A bacteriochlorin of Formula I:

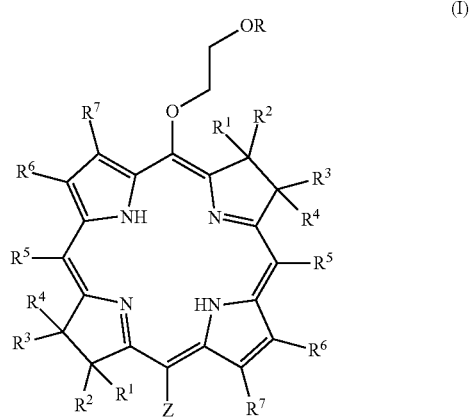

wherein:

R is H or silyl;

each $R^1$ and $R^2$ is independently selected from the group consisting of H, alkyl, aryl, alkoxy, halo, mercapto, cyano, hydroxyl, nitro, acyl, alkylthio, alkylamino, acyloxy, and —$C(O)NR_aR_b$ where $R_a$ and $R_b$ are each independently selected from the group consisting of alkyl, cycloalkyl, alkenyl, alkynyl and aryl, preferably H or alkyl;

each $R^3$ and $R^4$ is independently selected from the group consisting of alkyl, cycloalkyl, aryl, and arylalkyl;

each $R^5$ is independently selected from the group consisting of H, alkyl, alkenyl, alkynyl, cycloalkyl, aryl, arylalkyl, arylalkenyl, arylalkynyl, alkoxy, halo, cyano, nitro, acyl, alkylthio, alkylamino, arylalkylamino, disubstituted amino, acylamino, acyloxy, and —$C(O)NR_aR_b$ where $R_a$ and $R_b$ are each independently selected from the group consisting of alkyl, cycloalkyl, alkenyl, alkynyl and aryl;

each $R^6$ and $R^7$ is independently selected from the group consisting of H, alkyl, alkenyl, alkynyl, cycloalkyl, aryl, arylalkyl, arylalkenyl, arylalkynyl, halo, cyano, nitro, acyl, alkoxy, alkylthio, alkylamino, arylalkylamino, disubstituted amino, acylamino, acyloxy, —$C(O)NR_aR_b$ where $R_a$ and $R_b$ are each independently selected from the group consisting of alkyl, cycloalkyl, alkenyl, alkynyl and aryl, —$C(O)OR_c$ where $R_c$ is selected from the group consisting of alkyl, cycloalkyl, alkenyl, alkynyl, aryl, and C(O)OH; and Z is H or halo.

2. The compound of claim 1, wherein each $R^1$ and $R^2$ is independently selected from the group consisting of H and alkyl.

3. The compound of claim 1, wherein each $R^3$ and $R^4$ is independently selected alkyl.

4. The compound of claim 1, wherein each $R^5$ is H.

5. The compound of claim 1, wherein each $R^6$ is methylphenyl.

6. The compound of claim 1, wherein each $R^7$ is H.

7. The compound of claim 1, wherein Z is H.

8. The compound of claim 1, wherein Z is halo.

9. The compound of claim 1, wherein R is silyl.

10. The compound of claim 1 selected from the group consisting of:

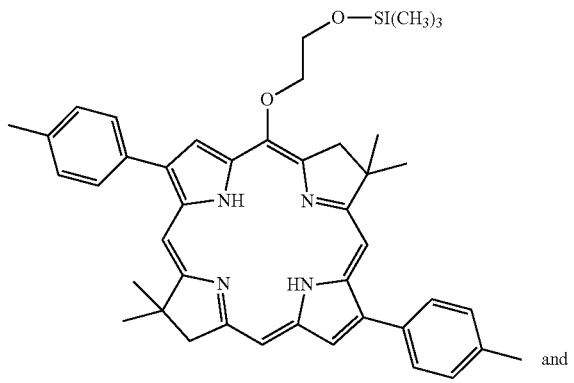

BC-3 and

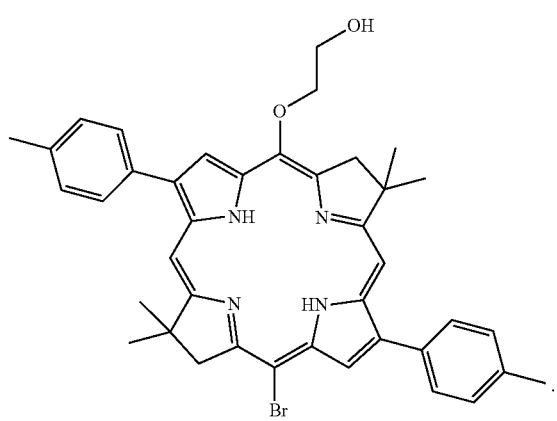

BC-5

11. The compound of claim 1, wherein R is trialkylsilyl.

12. The compound of claim 11, wherein Z is H.

13. A method of making a bacteriochlorin of claim 1, comprising:

condensing a pair of compounds of Formula II:

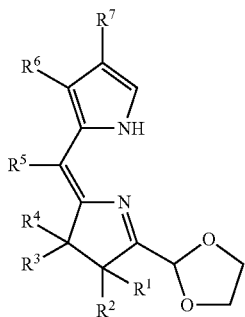

(II)

wherein each $R^1$, $R^2$, $R^3$, $R^4$, $R^5$, $R^6$ and $R^7$ is as given above;

in the presence of $CF_3SO_3R$ wherein R is silyl, to produce said bacteriochlorin of claim 1 wherein R is silyl.

14. The method of claim 13, further comprising the step of cleaving said silyl to produce said bacteriochlorin of claim 1 wherein R is H.

15. The method of claim 13, further comprising the step of halogenating said bacteriochlorin to produce a bacteriochlorin of claim 1 wherein Z is halo.

* * * * *